(12) United States Patent
Nielsen et al.

(10) Patent No.: US 8,062,253 B2
(45) Date of Patent: Nov. 22, 2011

(54) MEDICAL SKIN MOUNTABLE DEVICE

(75) Inventors: Ole Christian Nielsen, Hillerød (DK); Jim Radmer, Hillerød (DK); Jan Harald Preuthun, Bronshoj (DK)

(73) Assignee: Novo Nordisk A/S, Bagsvaerd (DK)

( * ) Notice: Subject to any disclaimer, the term of this patent is extended or adjusted under 35 U.S.C. 154(b) by 664 days.

(21) Appl. No.: 11/411,081

(22) Filed: Apr. 25, 2006

(65) Prior Publication Data
US 2006/0264835 A1    Nov. 23, 2006

Related U.S. Application Data

(63) Continuation of application No. PCT/DK2004/000726, filed on Oct. 21, 2004.

(60) Provisional application No. 60/518,836, filed on Nov. 10, 2003.

(30) Foreign Application Priority Data

Oct. 27, 2003   (EP) .................................. 03024626

(51) Int. Cl.
*A61M 37/00* (2006.01)
(52) U.S. Cl. ..................................... 604/131; 604/890.1
(58) Field of Classification Search ............... 604/890.1, 604/131–133, 65–67, 141, 156, 180, 181
See application file for complete search history.

(56) References Cited

U.S. PATENT DOCUMENTS

| 2,605,765 | A | 8/1952 | Kollsman |
|---|---|---|---|
| 3,406,686 | A | 10/1968 | Keller |
| 4,077,405 | A | 3/1978 | Haerten et al. |
| 4,140,117 | A | 2/1979 | Buckles et al. |
| 4,201,207 | A | 5/1980 | Buckles et al. |
| 4,340,048 | A | 7/1982 | Eckenhoff |
| 4,468,221 | A | 8/1984 | Mayfield |

(Continued)

FOREIGN PATENT DOCUMENTS

DE           2552446            5/1977

(Continued)

OTHER PUBLICATIONS

Non-Final Office Action Mailed Apr. 10, 2009 for U.S. Appl. No. 12/066,712 Filed Mar. 13, 2008; First Named Inventor: Steffen Hansen.

(Continued)

*Primary Examiner* — Christopher D Koharski
(74) *Attorney, Agent, or Firm* — Wesley A. Nicolas; Marc A. Began

(57) ABSTRACT

A medical device is provided comprising a transcutaneous device unit and a reservoir unit. The transcutaneous device unit comprises a transcutaneous device for transporting a fluid through a skin portion of a subject, and a mounting surface adapted for application to the skin of the subject. The reservoir unit comprises a reservoir adapted to contain a fluid drug, the reservoir comprising an outlet means allowing the transcutaneous device to be arranged in fluid communication with an interior of the reservoir, and an expelling assembly for expelling a fluid drug out of the reservoir and through the skin of the subject via the transcutaneous device. The transcutaneous device unit and the reservoir unit further comprise coupling means allowing the reservoir unit to be secured to the transcutaneous device unit in the situation of use. By this arrangement a two-unit system is provided which can be used in a convenient and cost-effective manner.

24 Claims, 16 Drawing Sheets

U.S. PATENT DOCUMENTS

| | | | |
|---|---|---|---|
| 4,552,561 A | 11/1985 | Eckenhoff et al. | |
| 4,562,751 A | 1/1986 | Nason et al. | |
| 4,685,903 A | 8/1987 | Cable et al. | |
| 4,811,845 A | 3/1989 | Baggett | |
| 4,886,499 A | 12/1989 | Cirelli et al. | |
| 4,898,582 A | 2/1990 | Faste | |
| 5,169,390 A | 12/1992 | Athayde et al. | |
| 5,256,157 A | 10/1993 | Samiotes et al. | |
| 5,257,980 A | 11/1993 | Van Antwerp et al. | |
| 5,487,738 A | 1/1996 | Sciulli | |
| 5,527,288 A | 6/1996 | Gross et al. | |
| 5,568,806 A | 10/1996 | Cheney, II et al. | |
| 5,616,132 A * | 4/1997 | Newman | 604/185 |
| 5,665,065 A | 9/1997 | Colman et al. | |
| 5,814,020 A | 9/1998 | Gross | |
| 5,858,001 A * | 1/1999 | Tsals et al. | 604/135 |
| 5,896,989 A | 4/1999 | Ropiak et al. | |
| 5,957,895 A | 9/1999 | Sage et al. | |
| 5,961,492 A | 10/1999 | Kriesel et al. | |
| 5,984,894 A | 11/1999 | Poulsen et al. | |
| 5,997,501 A | 12/1999 | Gross et al. | |
| 6,045,534 A * | 4/2000 | Jacobsen et al. | 604/156 |
| 6,068,613 A | 5/2000 | Kriesel et al. | |
| 6,074,369 A | 6/2000 | Sage et al. | |
| 6,200,293 B1 | 5/2001 | Kriesel et al. | |
| 6,248,093 B1 | 6/2001 | Moberg | |
| 6,251,098 B1 | 6/2001 | Rake et al. | |
| 6,280,148 B1 | 8/2001 | Zengerle et al. | |
| 6,287,289 B1 | 9/2001 | Niedospial, Jr. | |
| 6,290,678 B1 | 9/2001 | Aydelotte et al. | |
| 6,302,869 B1 | 10/2001 | Klitgaard | |
| 6,364,865 B1 * | 4/2002 | Lavi et al. | 604/411 |
| 6,485,471 B1 | 11/2002 | Zivitz et al. | |
| 6,500,150 B1 | 12/2002 | Gross et al. | |
| 6,554,798 B1 | 4/2003 | Mann et al. | |
| 6,589,369 B2 | 7/2003 | Yokoi et al. | |
| 6,622,037 B2 | 9/2003 | Kasano | |
| 6,764,567 B2 | 7/2004 | Sperko et al. | |
| 6,809,653 B1 | 10/2004 | Mann et al. | |
| 7,250,037 B2 | 7/2007 | Shermer et al. | |
| 2002/0040208 A1 | 4/2002 | Flaherty et al. | |
| 2002/0169416 A1 | 11/2002 | Gonnelli et al. | |
| 2002/0169439 A1 | 11/2002 | Flaherty | |
| 2003/0088238 A1 | 5/2003 | Poulsen et al. | |
| 2003/0135159 A1 | 7/2003 | Daily et al. | |
| 2003/0163090 A1 | 8/2003 | Blomquist et al. | |
| 2004/0059316 A1 | 3/2004 | Smedegaard | |
| 2004/0068230 A1 | 4/2004 | Estes et al. | |
| 2004/0092873 A1 | 5/2004 | Mober | |
| 2004/0122353 A1 | 6/2004 | Shahmirian et al. | |
| 2004/0138612 A1 | 7/2004 | Shermer et al. | |
| 2005/0022274 A1 | 1/2005 | Campbell et al. | |
| 2005/0065760 A1 | 3/2005 | Murtfeldt et al. | |
| 2005/0277884 A1 | 12/2005 | Kriesel et al. | |
| 2007/0088268 A1 | 4/2007 | Edwards | |

FOREIGN PATENT DOCUMENTS

| | | |
|---|---|---|
| DE | 4120267 | 12/1992 |
| EP | 1396275 | 3/2004 |
| EP | 1177802 | 9/2004 |
| EP | 1527792 | 5/2005 |
| EP | 1682203 | 5/2005 |
| EP | 1646412 | 6/2006 |
| EP | 1633414 | 4/2008 |
| JP | 2002-529204 | 9/2002 |
| WO | 92/22338 | 12/1992 |
| WO | WO9222338 | 12/1992 |
| WO | WO 96/14026 | 5/1996 |
| WO | WO0158506 | 8/2001 |
| WO | WO0240083 | 5/2002 |
| WO | WO0241999 | 5/2002 |
| WO | WO0029049 | 9/2002 |
| WO | WO02094352 | 11/2002 |
| WO | 03/026726 | 4/2003 |
| WO | WO03026726 | 4/2003 |
| WO | WO 03/037103 | 5/2003 |
| WO | WO 2004/056412 | 7/2004 |
| WO | WO2004110526 | 12/2004 |
| WO | WO 2005/002649 | 1/2005 |
| WO | WO 2005/011779 | 2/2005 |
| WO | WO2005039673 | 5/2005 |
| WO | WO2005072795 | 8/2005 |
| WO | WO2005077438 | 8/2005 |

OTHER PUBLICATIONS

Non-Final Office Action Mailed Oct. 27, 2009 for U.S. Appl. No. 12/066,712 Filed Mar. 13, 2008; First Named Inventor: Steffen Hansen.

Final Office Action Mailed Apr. 28, 2010 for U.S. Appl. No. 12/066,712 Filed March 13, 2008; First Named Inventor: Steffen Hansen.

Office Action Issued in Connection With Counterpart Danish Application No. PA 2005 00526 Mailed Jan. 30, 2006 for U.S. Appl. No. 11/911,213 Filed Oct. 11, 2007; First Named Inventor: Ole Christian Nielsen.

International Search Report and Written Opinion Issued In Connection With Counterpart International Application No. PCT/EP2006/061444 Mailed Aug. 9, 2006 for U.S. Appl. No. 11/911,213 Filed Oct. 11, 2007; First Named Inventor: Ole Christian Nielsen.

International Preliminary Examination Report Issued in Connection With Counterpart International Application No. PCT/EP2006/061444 Mailed Oct. 25, 2007 for U.S. Appl. No. 11/911,213 Filed Oct. 11, 2007; First Named Inventor: Ole Christian Nielsen.

Non-Final Office Action Mailed Jul. 24, 2009 in U.S. Appl. No. 11/911,213 Filed Oct. 11, 2007; First Named Inventor: Ole Christian Nielsen.

Non-Final Office Action Mailed Apr. 30, 2010 in U.S. Appl. No. 11/911,213 Filed Oct. 11, 2007; First Named Inventor: Ole Christian Nielsen.

English Abstract of DE 4120267.

Google Machine Translation of DE 2552446.

Google Machine Translation of Office Action Filed in Danish Application PA 2005 00526 Mailed Jan. 30, 2006..

Final Office Action Mailed Sep. 2, 2010 in U.S. Appl. No. 11/911,213 Filed Oct. 11, 2007; First Named Inventor: Ole Christian Nielsen.

Office Action Mailed Aug. 23, 2010 in U.S. Appl. No. 12/090,499 Filed Apr. 17, 2008; First Named Inventor: Karsten Kallesoe Nielsen.

English Abstract of JP2002-592204 Filed Sep. 10, 2002.

Non-Final Office Action Mailed Apr. 30, 2010 for U.S. Appl. No. 12/579,169 Filed Oct. 14, 2009; First Named Inventor: Ole Christian Nielsen.

Final Office Action Mailed Sep. 14, 2010 for U.S. Appl. No. 12/579,169 Filed Oct. 14, 2009; First Named Inventor: Ole Christian Nielsen.

* cited by examiner

MEDICAL SKIN MOUNTABLE DEVICE

CROSS REFERENCE TO RELATED APPLICATIONS

This Application is a continuation of International Application serial no. PCT/DK2004/000726 filed Oct. 21, 2004 and claims priority from European Application serial no. EP 03024626.8 filed Oct. 27, 2003 and to U.S. Provisional Application Ser. No. 60/518,836 filed Nov. 10, 2003.

FIELD OF THE INVENTION

The present invention generally relates to devices which are adapted for application to a skin surface of a subject and comprise a transcutaneous device for introduction of a fluid through the skin of the subject. In specific aspects, such devices may comprise a reservoir adapted to contain a fluid drug, and expelling means for expelling fluid drug out of the reservoir and through the skin of the subject via the transcutaneous device.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. Such devices are often termed infusion pumps.

Basically, infusion pumps can be divided into two classes. The first class comprises infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump)), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference. U.S. Pat. No. 6,364,865 discloses a manually held infusion device allowing two vial-type containers to be connected and a pressure to be build up in one of the containers to thereby expel a drug contained in that container.

The disposable pumps generally comprises a skin-contacting mounting surface adapted for application to the skin of a subject by adhesive means, and with the infusion needle arranged such that in a situation of use it projects from the mounting surface to thereby penetrate the skin of the subject, whereby the place where the needle penetrates the skin is covered while the appliance is in use. The infusion needle may be arranged to permanently project from the mounting surface such that the needle is inserted simultaneously with the application of the infusion pump, this as disclosed in U.S. Pat. Nos. 2,605,765, 4,340,048 and in EP 1,177,802, or the needle may be supplied with the device in a retracted state, i.e. with the distal pointed end of the needle "hidden" inside the pump device, this allowing the user to place the pump device on the skin without the possibility of observing the needle, this as disclosed in U.S. Pat. Nos. 5,858,001 and 5,814,020. In addition to pumps, alternative means for transporting a fluid drug may be used, e.g. iontophoresis as discussed below.

Although it can be expected that the above described second class of fully or partly disposable infusion devices can be manufactured considerably cheaper than the traditional durable infusion pump, they are still believed to be too expensive to be used as a real alternative to traditional infusion pumps for use on an every-day basis.

Before turning to the disclosure of the present invention, a different type of device relying on the insertion of a needle or needle-like structure will be described.

Although drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes.

A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned primarily with devices comprising a transcutaneous device such as a needle-formed sensor element.

The sensor may be placed subcutaneously being connected to external equipment by wiring or the substance (e.g. fluid) to be analysed may be transported to an external sensor element, both arrangements requiring the placement of a subcutaneous component (e.g. small catheter or tubing), the present invention addressing both arrangements. However, for simplicity the term "sensor" is used in the following for both types of elements introduced into the subject.

DISCLOSURE OF THE INVENTION

Having regard to the above-identified problems, it is an object of the present invention to provide a skin mountable drug delivery device or system and components therefore, which allow such a device or system to be used in a convenient and cost-effective manner. The configuration of the system and the components therefore should contribute in providing a medical delivery means which allows for easy and swift operation yet being reliable in use.

In the disclosure of the present invention, embodiments and aspects will be described which will address one or more of the above objects or which will address objects apparent from the below disclosure as well as from the description of exemplary embodiments.

Thus, corresponding to a first aspect, a medical device comprising a transcutaneous unit and a reservoir unit is provided, wherein the transcutaneous unit comprises transcutaneous means for transporting a fluid through a skin portion of a subject, and a mounting surface adapted for application to the skin of the subject. The reservoir unit comprises a reservoir adapted to contain a fluid drug, the reservoir comprising an outlet allowing the transcutaneous means to be arranged in fluid communication with an interior of the reservoir, and expelling means for, in a situation of use, expelling a fluid drug out of the reservoir and through the skin of the subject via the transcutaneous means. The transcutaneous unit and the reservoir unit further comprise coupling means allowing the reservoir unit to be secured to the transcutaneous unit in the situation of use.

The term "transcutaneous" covers all forms of administration in which a fluid is transported through a portion of the skin, e.g. intradermal or subcutaneous administration. The transcutaneous means may be in the form of a transcutaneous device, a jet injection means or electrodes allowing an ionic agent to permeate from a predetermined site on the surface of skin into the subcutaneous tissue of the subject by using the principle of iontophoresis. For a more thorough discussion of iontophoresis reference is made to U.S. Pat. No. 6,622,037 hereby incorporated by reference. Depending on the nature of the transcutaneous means the expelling means may be of different configuration and nature. For example, when one or more hollow infusion needles or cannulas are used, the expelling means may be arranged to force or suck the fluid drug from the reservoir, whereas in the case of iontophoresis the expelling means would be means for applying a current over a set of electrodes, i.e. "driving" means.

Corresponding to a further aspect, a medical device comprising a transcutaneous device unit and a reservoir unit is provided, wherein the transcutaneous device unit comprises a transcutaneous device, and a mounting surface for application to the skin of the subject. The reservoir unit comprises a reservoir adapted to contain a fluid drug, and an expelling assembly adapted for cooperation with the reservoir to expel the fluid drug out of the reservoir and through the skin of the subject via the transcutaneous device. The transcutaneous device unit and the reservoir unit are further adapted to be secured to each other in a situation of use thereby allowing a fluid communication to be established between the reservoir and the transcutaneous device. The transcutaneous device unit and the reservoir unit may comprise releasable coupling means allowing the reservoir unit to be secured to the transcutaneous device unit in a situation of us. Such a medical device comprising two units may also be considered a medical system. The transcutaneous device unit and the reservoir unit may each comprise a housing within which the transcutaneous device respectively the reservoir and the expelling assembly are arranged.

The term expelling assembly covers an aggregation of components or structures which in combination provides that a fluid can be expelled from the reservoir. The expelling assembly may e.g. be a mechanical pump (e.g. a membrane pump, a piston pump or a roller pump) in combination with electronically controlled actuation means, a mechanically driven pump (e.g. driven by a spring), a gas driven pump or a pump driven by an osmotic engine. The expelling assembly may also me in the form of an aggregation of components or structures which in combination provides that a fluid can be expelled from the reservoir when the expelling assembly is controlled or actuated by a controller external to the expelling assembly.

The transcutaneous device (which term also covers the similar terms transcutaneous access device and transcutaneous access tool traditionally used in this technical field) may be in the form of a pointed hollow infusion needle, a micro needle array, or a combination of a relatively flexible per se blunt cannula with a pointed insertion needle may provide a pointed transcutaneous device, the insertion needle being retractable after insertion of the blunt portion of the transcutaneous device. In the latter case the portion of the transcutaneous device actually placed in the subject and subsequently retracted by the herein described retraction means does not necessarily comprise a pointed end allowing the combined transcutaneous device to be inserted through the skin, such a pointed end being withdrawn during insertion of the transcutaneous device. The cannula is advantageously soft and flexible relative to the insertion needle which typically is a solid steel needle. In the disclosure of the present invention as well as in the description of the exemplary embodiments, reference will mostly be made to a transcutaneous device in the form of an infusion needle. The length of the transcutaneous device may be chosen in accordance with the actual application, e.g. a hollow steel needle which may be inserted at a substantially right angle relative to the skin surface may have an inserted length of 2-8 mm, preferably 3-5 mm, whereas a cannula which may also be inserted at an oblique angle relative to the skin surface may be somewhat longer, e.g. 4-20 mm.

The mounting surface is adapted for application against the skin of a subject (e.g. user or patient) and may be held in contact with the skin by attaching means external to the mounting surface (e.g. coupling means allowing the medical device to be coupled to a skin mountable device, or an adhesive bandage or a dressing) or by adhesive means provided on the mounting surface. The mounting surface may also be adapted for mounting towards the skin via an interposed component of a skin mountable device, e.g. a skin mountable device may comprise a receiving portion to which the medical device is attached, the transcutaneous device being inserted into the skin through an aperture in the receiving portion.

By the above arrangement different concepts can be realized. For example, by providing at least two different of one of the units, it will be possible to provided two or more combinations, wherein each combination of a transcutaneous device unit and a reservoir unit provides an assembly will have different capabilities as discussed in further detail below. In case the units are provided with releasable coupling means, one of the units can be exchanged with a new or different unit yet allowing the other unit to be re-used, thereby lengthening the operational life of the re-used unit. Thus, the present invention provides in an exemplary embodiment a device in which the components providing the interface with the user is incorporated in a first unit whereas the components providing the drug delivery per se is incorporated in a second unit, this allowing the combined components to be combined or exchanged in a simple, reliable and user-friendly way.

For example, the reservoir unit may be provided with an amount of drug and a delivery pump comprising an energy source allowing the drug to be delivered over e.g. 10 days, whereas the transcutaneous device unit may be provided with a transcutaneous device and an adhesive surface on the mounting surface having an expected (or recommended) operational life of 2 days, this allowing the reservoir unit to be used with 5 transcutaneous device units over a period of 10 days, this considerably lowering the total costs of using the combined device. The reservoir may be pre-filled or adapted to be filled one or more times.

On the other hand, a transcutaneous device unit may be provided with e.g. a needle or a soft cannula, and adhesive means (e.g. of the type used for attaching colostomy bags) allowing the needle unit to be mounted and used over an extended period of time, the reservoir unit having a shorter expected operational life, e.g. when relatively large amounts of drugs have to be infused. Alternatively, different reservoir units with different types of drugs may be used in combination with such a "long-term" mounted needle unit.

For ease of use, the fluid communication between the needle and the reservoir may be established when the needle unit and the reservoir unit are secured to each other, just as the expelling means may be activated when the needle unit and the reservoir unit are secured to each other and de-activated when the units are released from each other. Indeed, one or both of the operations may also be performed manually by the user.

In an exemplary embodiment the expelling assembly comprises a pump having an inlet adapted to be arranged in fluid communication with the outlet of the reservoir, and an outlet adapted to be arranged in fluid communication with the transcutaneous device, thereby allowing the transcutaneous device to be arranged in fluid communication with the interior of the reservoir. By such an arrangement the pump will serve as a suction pump drawing drug from the reservoir which consequently will have to be either collapsible or vented in case a non-collapsible reservoir is used. The expelling assembly may also be in the form of an arrangement adapted to pressurize the reservoir, e.g. an arrangement for driving a piston in a reservoir comprising a displaceable piston. The reservoir unit may comprise more than one reservoir and more than one expelling assembly. For example, a single expelling assembly may be used to expel drug from more than one reservoir, either simultaneously thereby mixing drugs or alternating, or each reservoir may be provided with an expelling assembly which may be connected to a common transcutaneous device or to individual transcutaneous devices, e.g. the transcutaneous device unit may comprise more than one transcutaneous device adapted to be connected to a expelling assembly.

In order to provide an initially sterile flow path through the pump, the flow path may be arranged between the inlet and outlet such that the inlet and outlet seal the interior of the pump and thereby the flow path in an initial sterile state. By this arrangement it will not be necessary to provide the reservoir unit as an entirely sterile unit—indeed, the drug will have to be provided in a sterile state.

In an exemplary embodiment, the reservoir unit is transformable from an initial condition in which there is no fluid communication between the pump and the reservoir to a non-reversible operating condition in which fluid communication is established between the inlet means of the pump and the outlet means of the reservoir when the pump unit is secured to a needle unit for the first time. By this arrangement it is avoided that undesired matter is introduced into the reservoir during re-connection between the pump and the reservoir.

To secure a clean connection between the pump and the reservoir, a separate fluid connector may be arranged within the interior of the pump in the initial condition. Such a fluid connector may comprise a pointed inlet end and an outlet, whereas the inlet of the pump and the outlet of the reservoir may be in the form of two needle-penetratable septa. By this arrangement the pointed end of the fluid connector, e.g. a connection needle, can be moved through the two septa and thus between the initial condition and an operating condition in which fluid communication is established between the interior of the reservoir and the interior of the pump via the fluid connector, the outlet of the fluid connector being arranged in the flow path. Advantageously the fluid connector is moved between its two positions as the reservoir unit is connected to a transcutaneous device unit for the first time. Correspondingly, during such a first connection two fluid communications will be established (between the transcutaneous device of the transcutaneous device and the pump, and between the pump and the reservoir), whereas during subsequent connections only a single new fluid communication will be established (between the transcutaneous device of the transcutaneous device unit and the pump).

In an exemplary embodiment the transcutaneous device comprises a first portion having a pointed distal end, and a second portion in fluid communication with the first portion and having a second end. Advantageously the second end of the transcutaneous device is pointed and the outlet means of the pump comprises a needle-penetratable septum allowing a fluid communication to be established between the second end of the transcutaneous device and the interior of the pump, preferably as the two units are connected to each other.

Correspondingly, in a further aspect the present invention provides a pump having an inlet means adapted to be arranged in fluid communication with a fluid supply, and an outlet means, the pump comprising an internal flow path arranged between the inlet and outlet means, the inlet and outlet means sealing the interior of the pump and thereby the flow path in an initial sterile condition, wherein a fluid connection means is arranged within the interior of the pump in the initial condition, the fluid connection means comprising an inlet end and an outlet, whereby the fluid connection means is arranged to be moved between the initial condition and to an operating condition in which the inlet end projects from the pump inlet means, whereby a fluid communication can be established between the fluid supply and the interior of the pump via the fluid connection means and with the outlet of the fluid connection means being arranged in the flow path.

The transcutaneous device unit may be supplied with e.g. a needle projecting from the mounting surface, however, to limit the risk of accidental needle injuries, the pointed end of the transcutaneous device is advantageously moveable between an initial position in which the pointed end is retracted relative to the mounting surface, and an extended position in which the pointed end projects relative to the mounting surface. Depending on the intended method of mounting the device on the user, the transcutaneous device may be moved between the two positions as the two units are connected to each, as would be appropriate in case the transcutaneous device unit is mounted on the skin of the user before the reservoir unit is connected. However, in case the two units are intended to be connected to each other before assembled units are mounted on the skin of the user, the transcutaneous device unit advantageously comprises user-actuatable actuation means for moving the pointed end of the transcutaneous device between the initial and the extended position.

To prevent inadvertent actuation of the transcutaneous device before the two units are assembled, the transcutaneous device unit may comprise means for blocking the actuation means, the blocking means being released when the transcutaneous device unit and the reservoir unit are secured to each other, thereby allowing the actuation means to be actuated.

To further reduce the likelihood of transcutaneous device injuries, the pointed end of the transcutaneous device may be moveable between the extended position in which the pointed end projects relative to the mounting surface, and a retracted position in which the pointed end is retracted relative to the mounting surface. Correspondingly, the combined device may comprise user-actuatable retraction means for moving the pointed end of the transcutaneous device between the extended and the retracted position when the retraction means is actuated. To prevent re-use of the transcutaneous device, the transcutaneous device may be permanently locked in its retraced position.

To prevent user-errors the actuation means for introducing the transcutaneous device may in an initial condition cover the retraction means, actuation of the actuation means uncovering the retraction means. For example, the actuation means may be in the form of gripping means (e.g. a strip) which is removed from the device, whereby removal triggers transcutaneous device insertion and at the same time uncovers the retraction for withdrawing the transcutaneous device.

As described above, the expelling assembly may be activated and deactivated when the two units are assembled and disassembled, however, the actuation and retraction means may also be used to activate respectively deactivate the expelling assembly. Just as for the initial connection between the pump and the reservoir, the initial activation of the expelling assembly may result in electronic control means being activated resulting in start of pumping action, whereas subsequent deactivation will only deactivate the actual pump action, the control means still being active (e.g. counting the time since initial activation of the control means).

In the above disclosure of the invention the two units have been described primarily as "unitary" units, however, this is only an exemplary configuration and these two "main" units may in case it is deemed desirable be subdivided into further units. For example, the reservoir unit may be provided with an exchangeable control unit, this allowing different types of control units to be connected to the reservoir unit per se. e.g. a first type of control unit may provide a single delivery profile, a second control unit may be programmable to thereby modify the delivery pattern, or a control third unit may comprise means allowing the control unit to communicate with external means. In the latter case the control unit may be controlled using a cordless remote control. Correspondingly, the reservoir may be exchangeable allowing different sizes of reservoirs or different types of drugs to be used.

In a further aspect of the invention, a transcutaneous device unit is provided as described above and being adapted to be used in combination with a reservoir unit as disclosed above. Correspondingly, the invention also provides a reservoir unit as disclosed above, the reservoir unit being adapted to be used in combination with a transcutaneous device unit as disclosed above. In an exemplary embodiment such a transcutaneous device unit may be provided with a hollow needle comprising a pointed distal end with an outlet opening-and being adapted to penetrate the skin of a subject, and a pointed proximal end with an inlet opening forming a fluid inlet means, the fluid inlet means being adapted to be arranged in fluid communication with a fluid supply. By this arrangement the needle provides a hydraulically stiff fluid communication between the needle inlet and outlet openings (e.g. made from metal), this allowing early occlusion detection by monitoring a pressure build-up upstream of the needle.

In a yet further aspect, a system is provided comprising a first needle unit and a first reservoir unit as disclosed above in combination with a least one further needle unit or reservoir unit as disclosed above, the further unit(s) having different capabilities than the first units. The different capabilities may relate to any constructional feature of the units, e.g. the type of needle, the type of user-actuatable means, the type of delivery/pump means, or the type of reservoir/drug.

More specifically, in an exemplary embodiment a system is provided comprising a transcutaneous device unit as disclosed above, and a plurality of reservoir units, each comprising a reservoir containing a fluid drug, and an expelling assembly for expelling fluid drug from the reservoir. The transcutaneous device unit and the reservoir units comprise mating coupling means allowing a reservoir unit to be secured to the transcutaneous device unit to provide fluid communication between the reservoir and the transcutaneous device, wherein each combination of a transcutaneous device unit and a reservoir unit provides an assembly having different capabilities. The different capabilities may be realized providing e.g. reservoir units with different amounts of the same drugs, reservoir units with different drugs or variants of a given drug, reservoir units adapted to expel drug at different preset rates, reservoir units adapted to expel at fixed respectively selectable rates. One of the reservoir units may be provided with a processor controlling the expelling assembly and a receiver operatable coupled to the controller for receiving flow instructions from a separate control device and delivering the flow instructions to the processor. The receiver may be a wireless receiver. The reservoir units may further be provided with different input means (e.g. for wireless or non-wireless connection, or manual input), or different output means (e.g. for wireless or non-wireless connection, different display means, or different alarm means).

In a further exemplary embodiment, a system is provided comprising a plurality of transcutaneous device units as described above, and a reservoir unit comprising a reservoir containing a fluid drug, and an expelling assembly for expelling fluid drug from the reservoir. The transcutaneous device units and the reservoir unit comprise mating coupling means allowing a transcutaneous device unit to be secured to the reservoir unit to provide fluid communication between the reservoir and the transcutaneous device, wherein each combination of a transcutaneous device unit and a reservoir unit provides an assembly having different capabilities. The different capabilities may be realized by providing the transcutaneous device units with different transcutaneous devices such as a hollow subcutaneous needle, a cannula and insertion needle assembly, and a micro needle array, by providing different adhesives, by providing different insertion or retraction means, or by providing different coupling means.

In a yet further exemplary embodiment, a system is provided comprising a transcutaneous device unit comprising a transcutaneous device and a mounting surface adapted for application to the skin of a subject, a reservoir unit comprising a reservoir containing a fluid drug, and at least a portion of an expelling assembly for expelling fluid drug from the reservoir, and a plurality of control units, each comprising a controller for controlling an expelling assembly, each having different capabilities. The transcutaneous device unit and the reservoir unit comprise mating coupling means allowing the reservoir unit to be secured to the transcutaneous device unit to provide fluid communication between the reservoir and the transcutaneous device, and the controller units and the reservoir unit comprise mating coupling means allowing a controller unit to be secured to the reservoir unit to control the expelling assembly, whereby each combination of a transcutaneous device unit, a reservoir unit and a control unit provides an assembly having different capabilities. The control units may have different control functions as described above in respect of a system comprising a plurality of reservoir units. In an alternative configuration the reservoir unit and the transcutaneous device unit may be provided as a unitary structure adapted to cooperate with the control unit.

The present invention also provides a method comprising the steps of providing a transcutaneous device unit comprising a transcutaneous device and a mounting surface, providing a reservoir unit comprising a reservoir adapted to contain a fluid drug, and an expelling assembly for expelling fluid drug from the reservoir, the method comprising the further step of assembling the transcutaneous device unit and the reservoir unit to provide a fluid communication between the reservoir and the transcutaneous device. The fluid communication between the transcutaneous device and the reservoir may be established when the two units are assembled or it may be established when the assembled device is further actuated, both options being covered by the above definition. The method may comprise the further steps of mounting the mounting surface to a skin surface of a subject, and, after mounting the mounting surface to the skin surface of the subject, actuating the transcutaneous device to establish a fluid communication between the reservoir and the subject.

A further method provides a drug delivery device dispensing a drug at a preset rate, the method comprising the steps of providing a system comprising a transcutaneous device unit comprising a transcutaneous device and a mounting surface adapted for application to the skin of a subject, the system further comprising a plurality of reservoir units, each comprising a reservoir containing a fluid drug, and an expelling assembly for expelling fluid drug from the reservoir at a preset rate, selecting a reservoir unit having a desired preset rate, and assembling the transcutaneous device unit and the selected reservoir unit to provide a fluid communication between the reservoir and the transcutaneous device.

In the above disclosure the present invention has been described with reference to a drug delivery device, however, the concept of the invention can be regarded as a modular system providing a number of advantages. Thus, the transcutaneous device unit may also be in the form of a needle sensor and the "reservoir unit" may correspondingly be in the form of a device adapted to transmit and/or process data acquired via the sensor.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject. Further, the term needle (when not otherwise specified) defines a piercing member adapted to penetrate the skin of a subject.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Firstly, with reference to FIGS. 1-12 an embodiment of a drug delivery device will be described focusing primarily on the directly user-oriented features. The transcutaneous device unit 2 comprises a transcutaneous device in the form of a hollow infusion needle and will thus in the following be termed a needle unit, however, the needle may be replaced with any desirable transcutaneous device suitable for delivery of a fluid drug.

Figure 1:
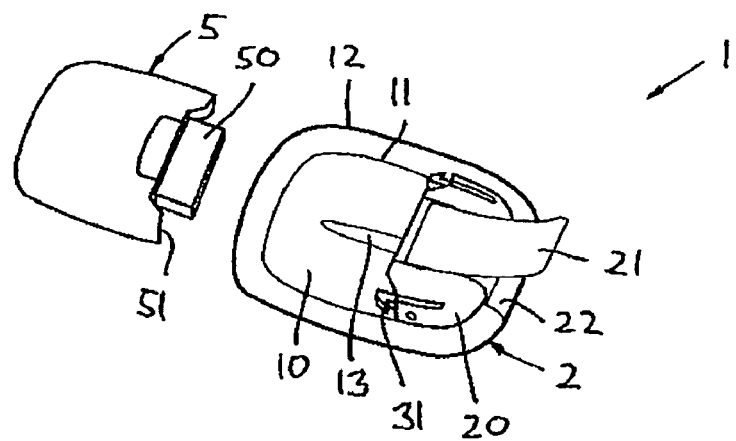
FIGS. 1-11 shows in perspective views the sequences of use for a first embodiment of a drug delivery device.

More specifically, FIG. 1 shows a perspective view of medical device in the form of a modular skin-mountable drug delivery device 1 comprising a patch-like needle unit 2 and a reservoir unit 5. When supplied to the user each of the units are preferably enclosed in its own sealed package (not shown).

The needle unit comprises a base portion 10 with a lower mounting surface adapted for application to the skin of a user, and a housing portion 20 in which a hollow infusion needle (not shown) is arranged. The needle comprises a first needle portion having a pointed distal end adapted to penetrate the skin of a user, and a second pointed end adapted to be arranged in fluid communication with the reservoir unit. In the shown embodiment the pointed end of the needle is moveable between an initial position in which the pointed end is retracted relative to the mounting surface, and an extended position in which the pointed end projects relative to the mounting surface. Further, the needle is moveable between the extended position in which the pointed end projects relative to the mounting surface, and a retracted position in which the pointed end is retracted relative to the mounting surface. The needle unit further comprises user-gripable actuation means in the form of a first strip-member 21 for moving the pointed end of the needle between the initial and the second position when the actuation means is actuated, and user-gripable retraction in the form of a second strip-member 22 means for moving the pointed end of the needle between the extended and the retracted position when the retraction means is actuated. As can be seen, the second strip is initially covered by the first strip. The housing further comprises user-actuatable male coupling means 40 in the form of a pair of resiliently arranged hook members adapted to cooperate with corresponding female coupling means on the reservoir unit, this allowing the reservoir unit to be releasable secured to the needle unit in the situation of use. In the shown embodiment the base portion comprises a relatively rigid upper portion 11 attached to a more flexible adhesive sheet member 12 having a lower adhesive surface providing the mounting surface per se, the adhesive surface being supplied with a peelable protective sheet. The base portion also comprises a ridge member 13 adapted to engage a corresponding groove on the reservoir unit.

The reservoir unit 5 comprises a pre-filled reservoir containing a liquid drug formulation (e.g. insulin) and expelling means in the form of an electronically controlled pump for expelling the drug from the reservoir through the needle in a situation of use. The reservoir unit has a generally flat lower surface adapted to be mounted onto the upper surface of the base portion, and comprises a protruding portion 50 adapted to be received in a corresponding cavity of the housing portion 20 as well as female coupling means 51 adapted to engage the corresponding hook members 31 on the needle unit. The protruding portion provides the interface between the two units and comprises a pump outlet and contact means (not shown) allowing the pump to be started as the two units are assembled. The lower surface also comprises a window (not to be seen) allowing the user to visually control the contents of the reservoir.

Figure 2:
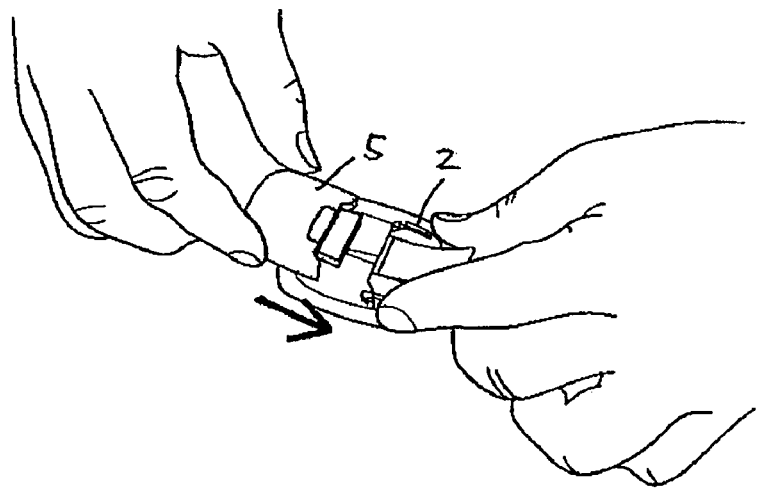
Figure 3:
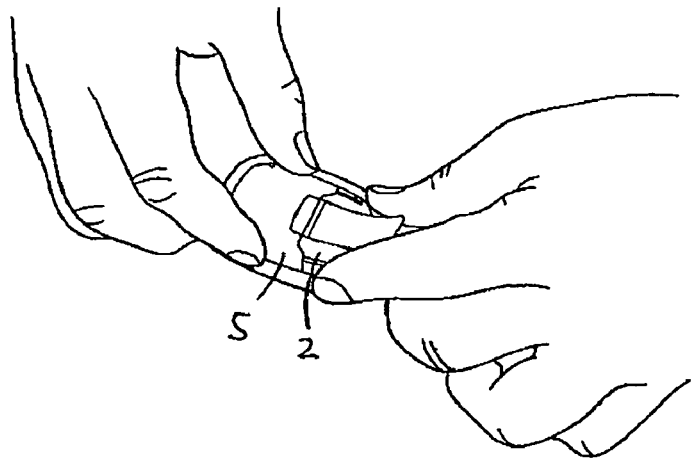
Figure 4:
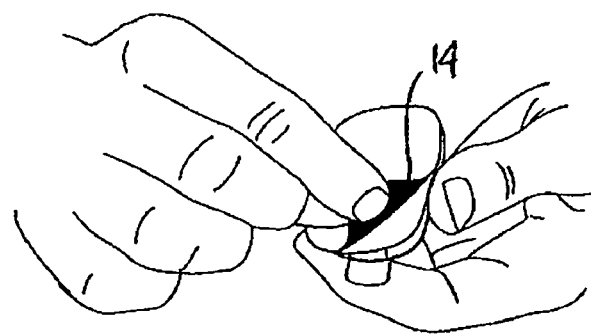
Figure 5:
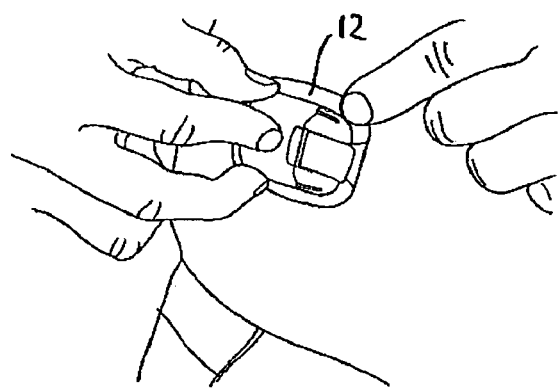
Figure 6:
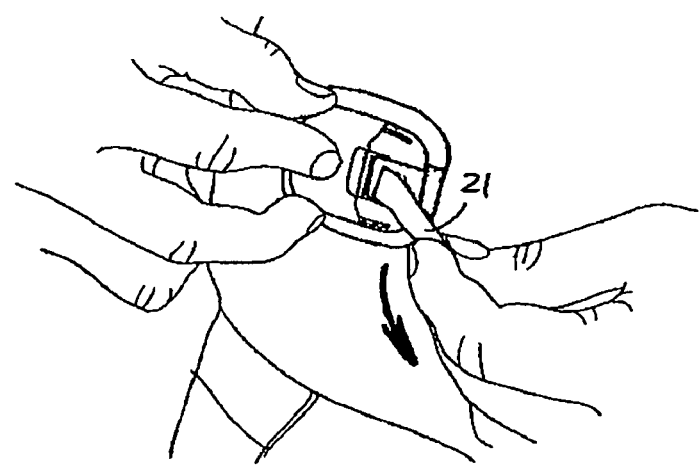
Figure 7:
Figure 8:
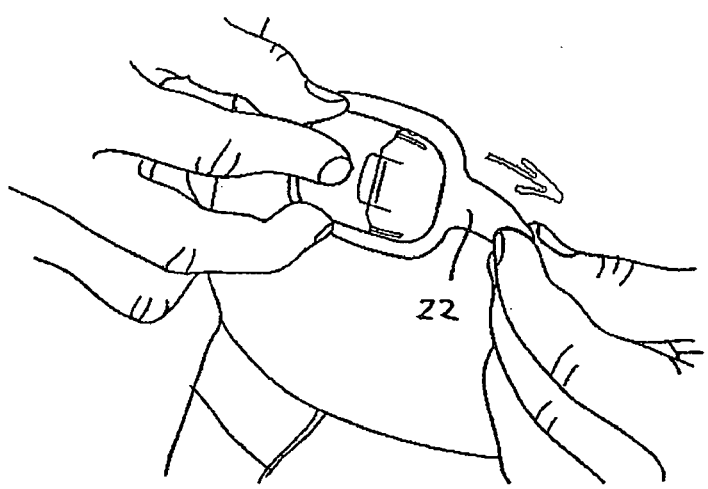

First step in the mounting procedure is to assemble the two units by simply sliding the reservoir unit into engagement with the needle unit (FIG. 2). When the hook members properly engage the reservoir unit a "click" sound is heard (FIG. 3) signalling to the user that the two units have been properly assembled. If desired, a visual or audible signal may also be generated. Thereafter the user removes the peelable sheet 14 to uncover the adhesive surface (FIG. 4) where after the device can be attached to a skin surface of the user, typically the abdomen (FIG. 5). Infusion of drug is started by gripping and pulling away the actuation strip 21 as indicated by the arrow whereby the needle is inserted followed by automatic start of the infusion (FIG. 6). The needle insertion mechanism may be supplied in a pre-stressed state and subsequently released by the actuation means or the needle insertion may be "energized" by the user. A "beep" signal confirms that the device is operating and drug is infused. The reservoir unit is preferably provided with signal means and detection means providing the user with an audible alarm signal in case of e.g. occlusion, pump failure or end of content.

Figure 9:
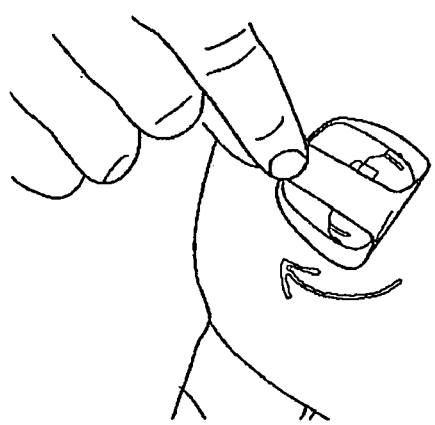
Figure 10:
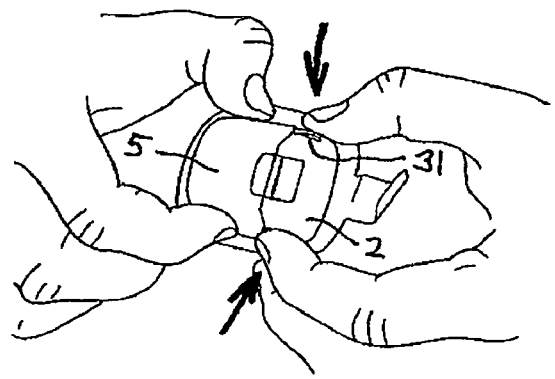
Figure 11:
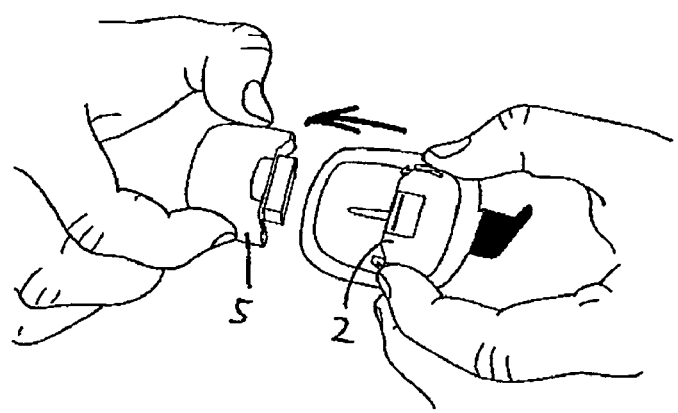
Figure 12:
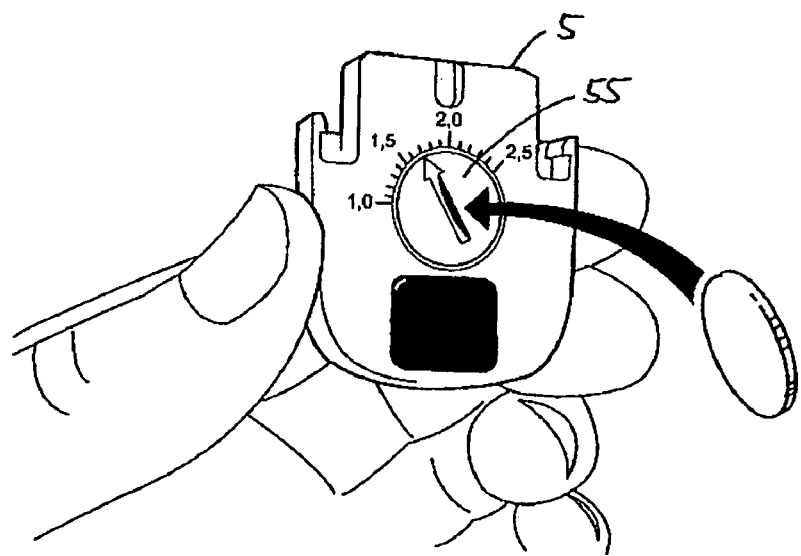
FIG. 12 shows a further embodiment of a reservoir unit.

After the device has been left in place for the recommended period of time for use of the needle unit (e.g. 48 hours)—or in case the reservoir runs empty or for other reasons—it is removed from the skin by gripping (FIG. 7) and pulling (FIG. 8) the retraction strip 22 as indicated by the arrows which leads to retraction of the needle followed by automatic stop of drug infusion where after the strip which is attached to the adhesive patch is used to remove the device from the skin surface (FIG. 9).

When the device has been removed the two units are disengaged by simultaneously depressing the two hook members 31 as indicated by the arrows (FIG. 10) allowing the reservoir unit 5 to be pulled out of engagement with the needle unit 2 as indicated by the arrow (FIG. 11) which can then be discarded. Thereafter the reservoir unit can be used again with fresh needle units until it has been emptied.

The reservoir unit may be supplied with a fixed basal infusion rate or it may be supplied as an adjustable unit (FIG. 12) with adjustment means 55 allowing the infusion rate to be set by a physician and/or the user/patient. The reservoir unit may also be provided with means allowing the control means to be programmed or set electronically (not shown).

The device described with reference to FIGS. 1-11 may also be used in alternative ways. For example, the needle unit may be mounted to the skin after which the reservoir is attached. Depending on the configuration of the needle unit, it may be possible or prevented that the needle is introduced before the reservoir unit is attached.

Figure 13:
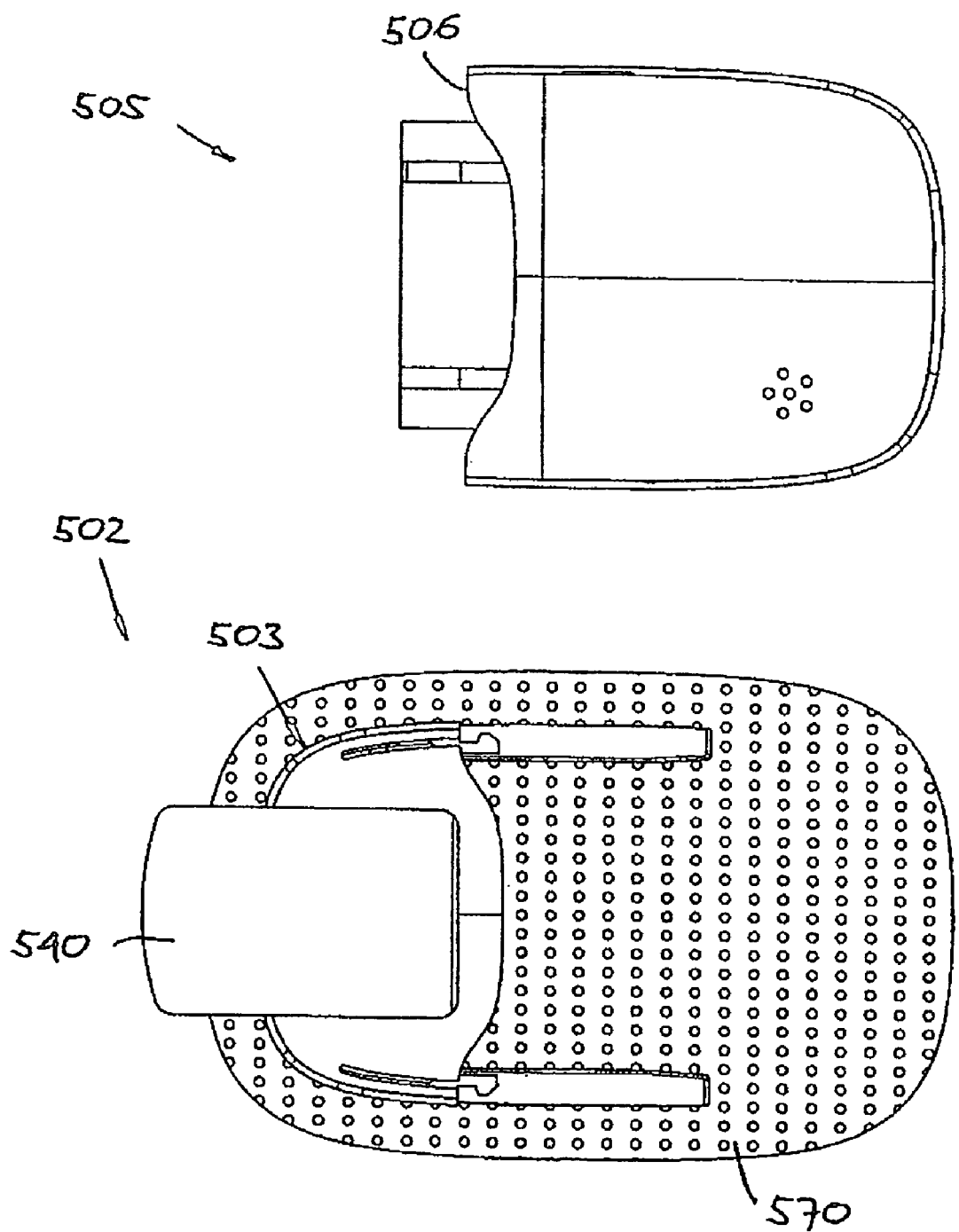
FIG. 13 shows in a non-assembled state a needle unit and a reservoir unit for a further embodiment of a drug delivery device.

FIG. 13 shows a further embodiment of medical device 500 substantially corresponding to the embodiment of FIG. 1, the device comprising a patch-like needle unit 502 and a thereto attachable reservoir unit 505.

Figure 14:
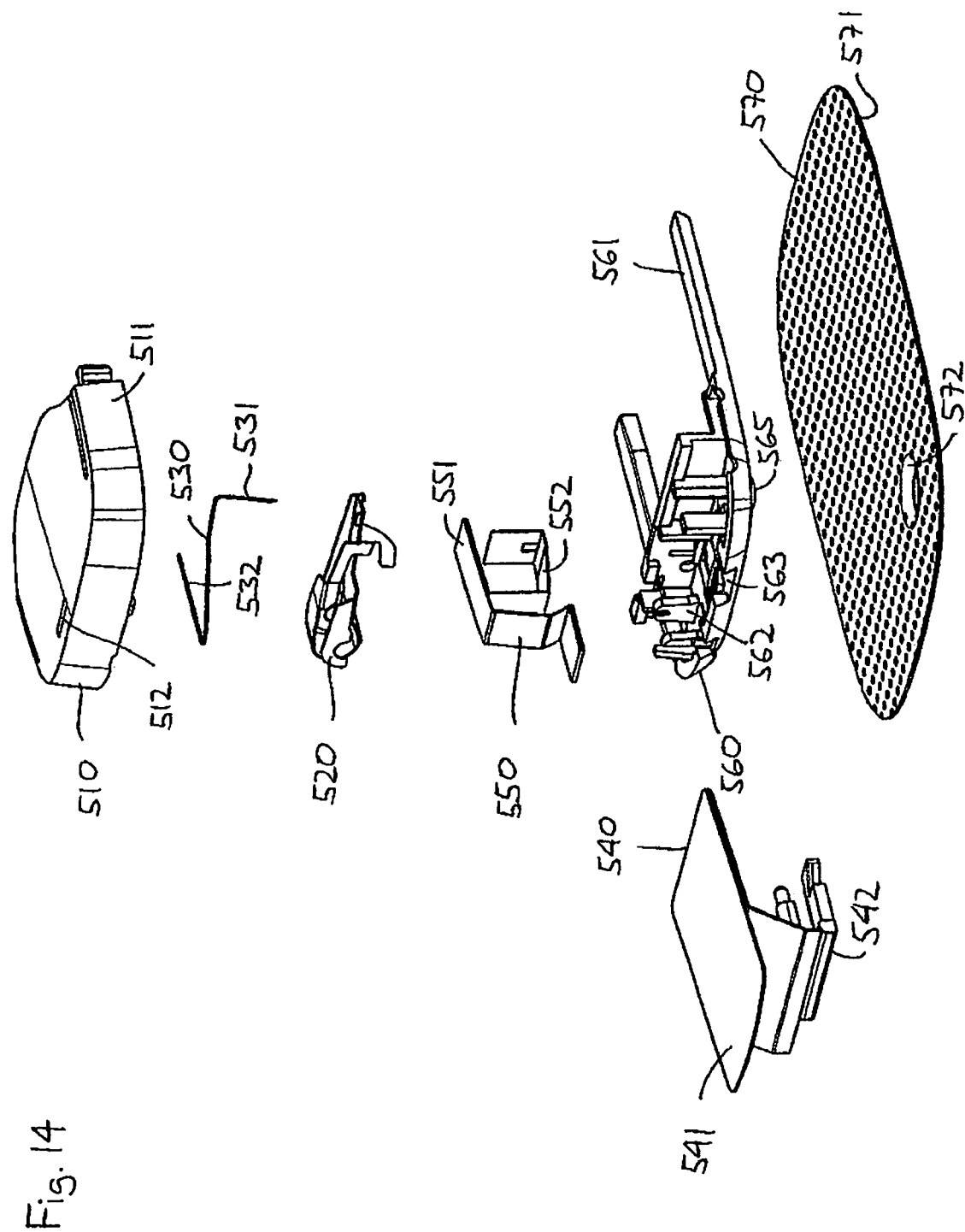
FIG. 14 shows an exploded view of the needle unit of FIG. 13.
Figure 15:
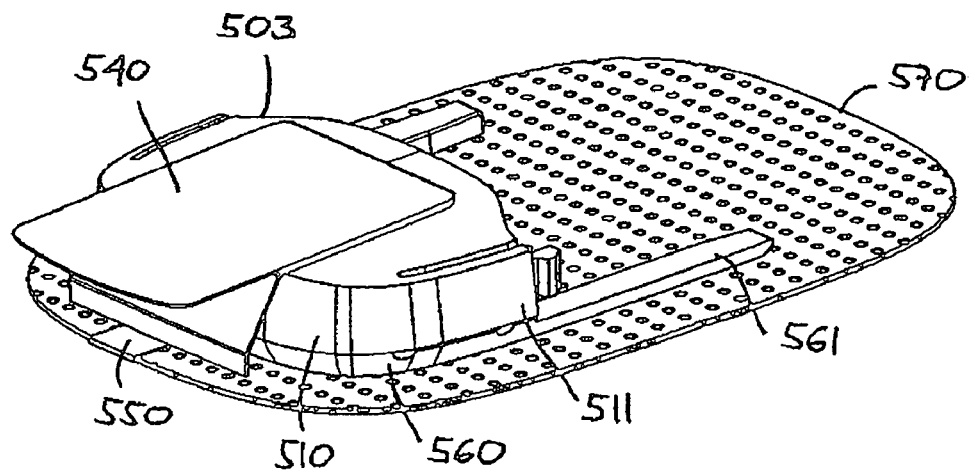
FIG. 15 shows a perspective view of the needle unit of FIG. 13 in a first state.

FIG. 14 shows an exploded perspective view of the needle unit comprising an upper housing portion 510, a needle carrier 520 and a thereto mounted infusion needle 530, an actuation member 540, a release member 550, a lower housing portion 560 and a sheet member 570. The actuation member comprises a user gripable portion 541 and a needle actuation portion 542, and the release member comprises a user gripable portion 551 and a needle retraction portion 552. In the assembled state as shown in FIG. 15, the upper and lower housing portions form a housing 503 in which the needle and the needle carrier is mounted, the actuation and release members being operatable connected to the needle carrier with the user gripable portions arranged outside the housing. In contrast to the FIG. 1 embodiment does the needle unit not comprise a base plate portion but instead two ridge members 561 extending from the housing, the ridge members and the lower surface of the housing being mounted on the flexible sheet member which is provided with a lower adhesive layer 571 on its lower surface allowing the needle unit to be attached to a skin site of a subject. The sheet member further comprises an opening 572 arranged in register with a lower protrusion 565 provided around the exit aperture for the transcutaneous device, just as the sheet is provided with a large number of small perforations to improve breathability through the sheet. The housing 503 is provided with user actuatable coupling means 511 allowing a reservoir unit to be attached to and released from the needle unit 505, the reservoir unit comprising corresponding mating coupling means 506 as well as a display 587. The display may indicate e.g. proper function of the unit, the amount of drug in the reservoir or different error conditions.

As seen is the user gripable portion 551 of the release member initially covered by a portion of the actuation member, this reducing the probability that the user erroneously uses the release member instead of the actuation member. Further, the actuation and release members (or portion thereof) may be colour coded to further assist the user to correctly use the device. For example, the actuation member may be green to indicate "start" whereas the release member may be red to indicate "stop".

Figure 16:
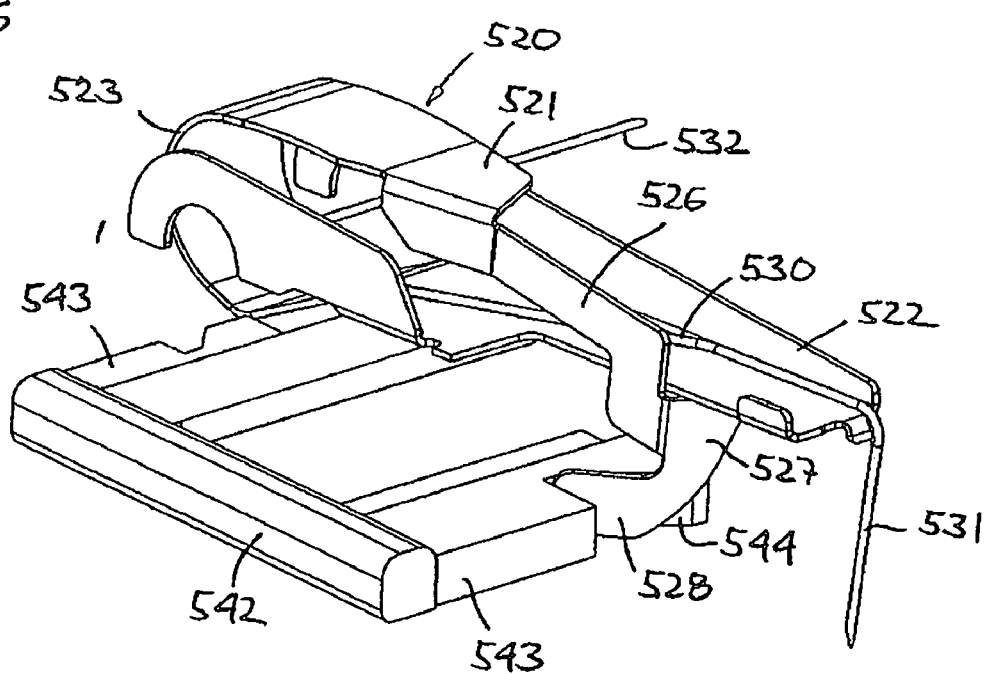
FIG. 16 shows a perspective view of the needle carrier of FIG. 14.

FIG. 16 shows in perspective the needle carrier 520 with the needle 530 and the needle actuation portion 542 of the actuation member 540. The needle actuation portion comprises two legs 543 allowing it to slide relative to the housing, the legs being arranged through respective openings 563 in the housing. The needle carrier is adapted to be connected to a hinge member 562 of the lower housing portion to thereby allow the needle carrier and thereby the needle to pivot corresponding to a pivoting axis defined by a hinge. In the shown embodiment is the needle carrier in the form a bent sheet metal member, the carrier comprising an upper arm 521 and a lower arm 522 connected to each other by a hinge portion 523 allowing the lower arm to pivot relative to the upper arm and corresponding to the pivoting axis. The lower arm forms a tray in which the hollow infusion needle 530 is mounted (e.g. by welding or adhesive), the needle having a distal pointed portion 531 adapted to penetrate the skin of the subject, the distal portion extending generally perpendicular to the mounting surface of the needle unit, and a proximal portion 532 arranged substantially corresponding to the pivoting axis and adapted to engage a fluid supply. Thus, when a portion of the upper arm is mounted in the housing, the lower arm can pivot between a first retracted position in which the distal portion of the needle is retracted within the housing, and a second extended position in which the distal portion projects relative to the mounting surface. In the shown embodiment the needle carrier provides the drive means for moving the lower arm between the two positions.

This may as in the present embodiment be provided by the elastic properties of the sheet material per se corresponding to the hinge portion, or alternatively an additional spring may be provided between the two arms to thereby urge them apart. To lock the lower part in an energized, releasable first position, the upper arm is provided with a flexible release arm 526 comprising a catch 527 supporting and arresting the lower arm in its first downwardly biased position, as well as a release portion 528 engaging a ramp surface 544 of the needle actuation portion 542, the catch further comprising an inclined edge portion 529 adapted to engage the lower arm when the latter is moved from its extended to its retracted position as will be described in greater detail below.

Figure 17:
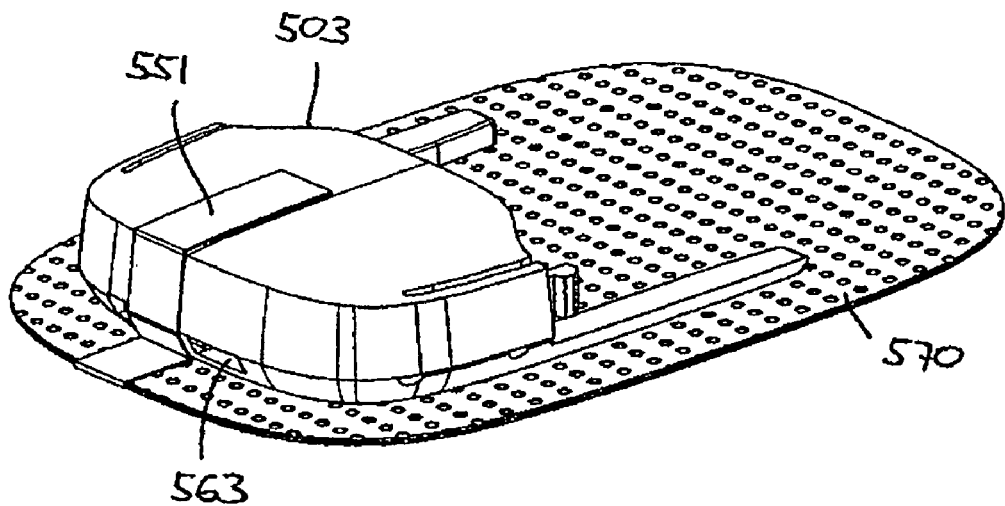
FIG. 17 shows a perspective view of the needle unit of FIG. 13 in a second state.

To actuate the needle the user grips the flexible strip forming the user gripable portion 541 (which preferably comprises adhesive portions to hold it in its shown folded initial position) and pulls the needle actuation portion 542 out of the housing, the actuation member 540 thereby fully disengaging the housing. More specifically, when the ramp surface 544 is moved it forces the latch 527 away from the lower arm to thereby release it, after which the release portion 528 disengages the ramp allowing the two legs to be pulled out of the housing. As seen in FIG. 17, when the actuation member is removed the user gripable portion 551 of the release member is exposed. As for the actuation member, the user gripable portion of the release member preferably comprises adhesive portions to hold it in its shown folded initial position.

Figure 18:
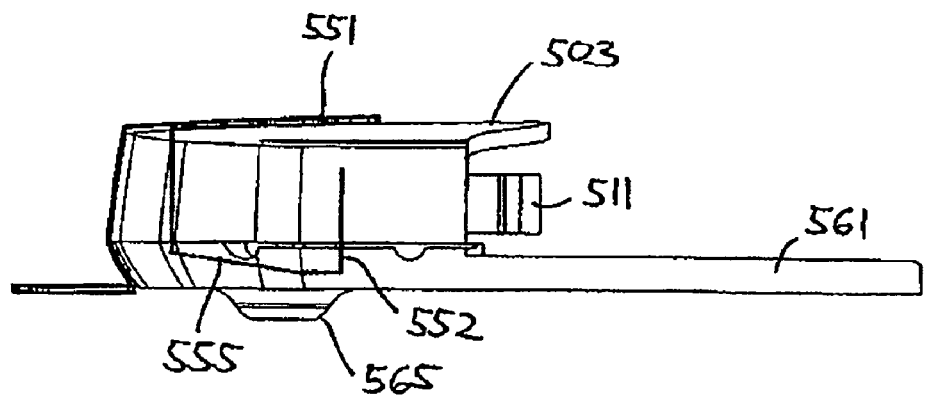
FIG. 18 shows a side view of the needle unit of FIG. 13.

In the shown embodiment the release member is in the form of a strip formed from a flexible material and having an inner and an outer end, the strip being threaded through an opening 512 in the housing, the strip thereby forming the user gripable portion 551 and the needle retraction portion 552, the inner end of the strip being attached to the housing and the outer end of the strip being attached to a peripheral portion of the sheet member 570 or, alternatively, a peripheral portion of the housing. In the projection shown in FIG. 18 the release member is shown in its initial position, the retraction portion forming a loop 555 arranged below the lower arm of the needle carrier, this position allowing the lower arm to be moved to its actuated position and thereby the needle to its extended position.

When the user decides to remove the needle unit from the skin, the user grips the user gripable portion 551, lifts it away from the housing and pulls it upwardly whereby the loop shortens thereby forcing the lower arm upwardly, this position corresponding to an intermediate release state. By this action the lower arm engages the inclined edge portion 529 of the catch 527 thereby forcing it outwardly until it snaps back under the lower arm corresponding to the position shown in FIG. 16. As the actuation member 540 has been removed from the needle unit, the needle carrier is irreversibly locked in its retracted position. When the user further pulls in the release member, the peripheral portion of the sheet member to which the release member is attached will be lifted off the skin, whereby the needle unit with its attached reservoir unit can be removed from the skin, this as shown and described with reference to FIGS. 7-9.

Advantageously, the actuation and release members may be formed and arranged to communicate with the reservoir unit (not shown). For example, one of the legs of the actuation member may in its initial position protrude through the housing to thereby engage a corresponding contact on the reservoir unit, this indicating to the reservoir unit that the needle unit has been attached, whereas removal of the actuation member will indicate that the needle has been inserted and thus that drug infusion can be started. Correspondingly, actuation of the release member can be used to stop the pump.

Figure 19:
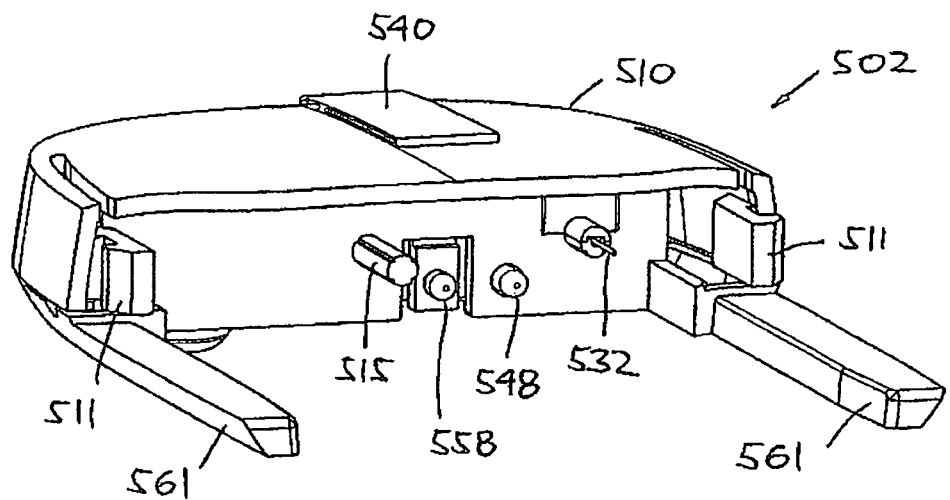
FIG. 19 shows a further perspective view of the needle unit of FIG. 13.

In FIG. 19 the side of the needle unit 502 which connects to the reservoir unit is shown. In addition to the two ridge members 561 and the user actuatable coupling means 511 the needle unit comprises further structures which connects to and/or engages the reservoir unit to provide a functional interface with the reservoir unit. More specifically, the needle unit comprises a fluid inlet provided by the pointed proximal portion 532 of the needle projecting from the needle unit and adapted to engage a fluid outlet of the reservoir unit, an actuator 515 projecting from the needle unit and adapted to engage and actuate a fluid connector in the reservoir unit (see below), and first and second contact actuators 548, 558 adapted to engage corresponding contacts on the reservoir unit. The first contact actuator is provided by the distal end of one of the legs 543 of the needle actuator projecting through an opening in the housing, and the second contact actuator is provided by a hinged portion of the housing connected to the needle retraction portion 552 of the release member 550. When the needle unit is first connected to the reservoir unit both contact actuators will protrude from the housing and engage the corresponding contacts on the reservoir unit thereby indicating that that a needle unit has been connected. When the needle is actuated the first contact actuator will be withdrawn and thereby disengage the corresponding contact on the reservoir unit to start pump actuation. When the needle is retracted the second contact actuator will pivot and disengage the corresponding contact on the reservoir unit to stop pump actuation.

Figure 20:
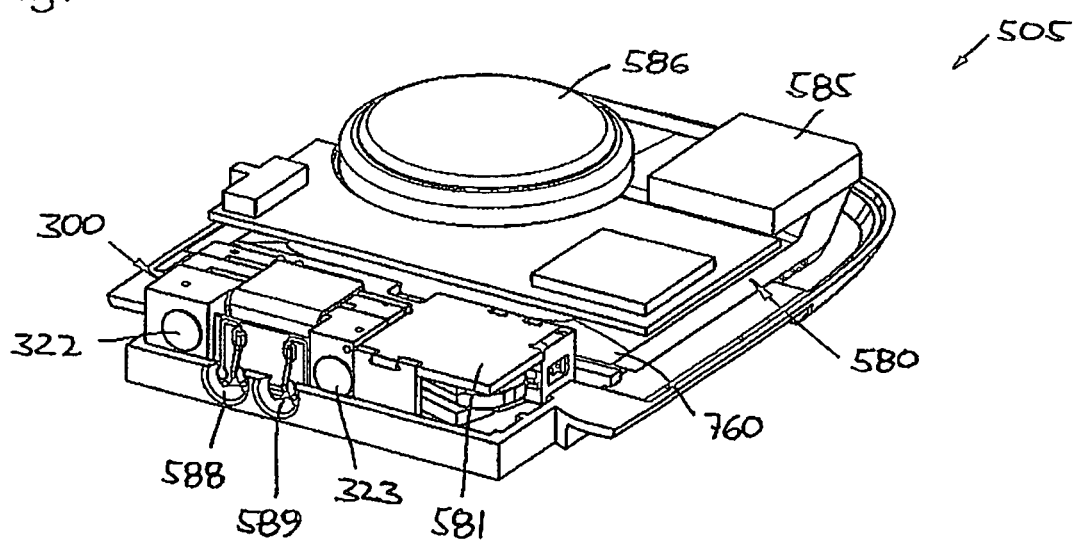
FIG. 20 shows perspective view of the interior of the reservoir unit of FIG. 13.

FIG. 20 shows the reservoir unit with an upper portion of the housing removed. The reservoir unit comprises a reservoir 760 and an expelling assembly comprising a pump assembly 300 and control and actuation means 580, 581 therefore. The pump assembly comprises an outlet 322 for connection to a transcutaneous access device (e.g. the needle 530) and an opening 323 allowing an internal fluid connector to be actuated, see below. The reservoir 560 is in the form of prefilled, flexible and collapsible pouch comprising a needle-penetratable septum adapted to be arranged in fluid communication with the pump assembly, see below. The shown pump assembly is a mechanically actuated membrane pump, however, the reservoir and expelling means may be of any suitable configuration, e.g. as disclosed with reference to FIGS. 25A-25D.

The control and actuation means comprises a pump actuating member in the form of a coil actuator 581 arranged to actuate a piston of the membrane pump, a PCB or flex-print to which are connected a microprocessor 583 for controlling, among other, the pump actuation, contacts 588, 589 cooperating with the contact actuators on the needle unit, signal generating means 585 for generating an audible and/or tactile signal, a display (not shown) and an energy source 586. The contacts are preferably protected by membranes which may be formed by flexible portions of the housing.

Figure 21:
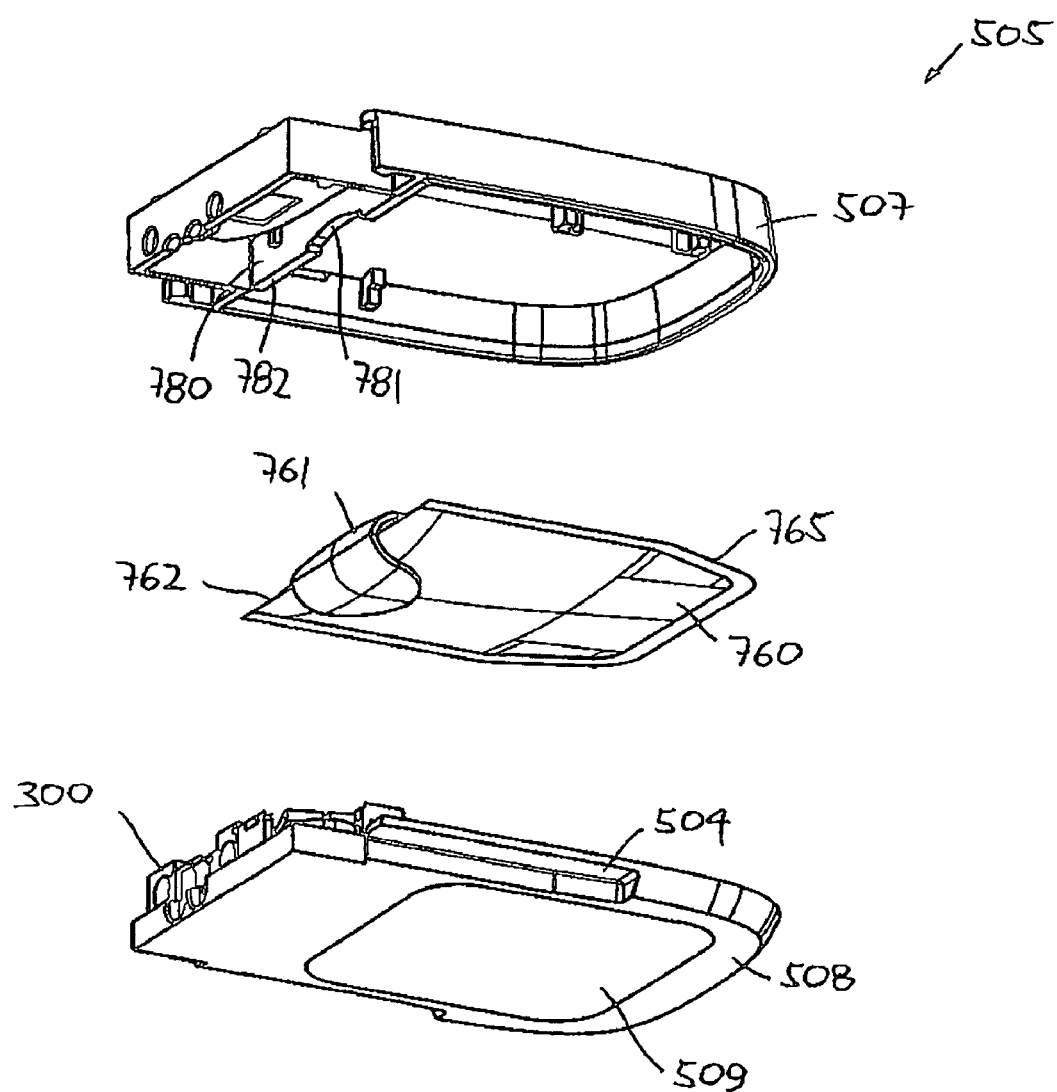
FIG. 21 shows an exploded view of a further reservoir unit.

In FIG. 21 an exploded view of the reservoir unit 505 of FIG. 13 is shown, the unit comprising an upper housing member 507, a lower housing member 508 with a transparent area 509 and grooves 504 to receive the ridge members 561 extending from the needle unit, a flexible reservoir 760 with a rounded edge portion 762 on which a septum member 761 is mounted, a pump assembly 300 with actuator and a circuit board (not shown) arranged above the reservoir and comprising electronic components for controlling actuation of the pump. The upper and lower housing members comprise reservoir mounting means in the form of opposed upper and lower ridge portions 780 (the lower not seen) adapted to engage and mount the reservoir in the housing. Each ridge portion comprises a central cut-out portion 781 adapted to engage the septum member on its opposed surfaces when the housing members are assemble thereby locking the reservoir in place within the housing. The degree of locking will be determined by the pressure exerted on the septum member, the elastic properties of the septum member and the friction between the ridge and the septum member. On each side of the cut-out portion the ridge portions comprise a straight portion 782 which may aid in mounting the reservoir in the housing. The straight portions may engage the initially prefilled reservoir to help lock it in place, however, as the reservoir is emptied and flattens this grip may lessen. In contrast, the engagement with the septum is adapted to lessen. In contrast, the engagement with the septum is adapted to properly hold the reservoir in place as the reservoir is emptied. The straight portions may also be adapted to pinch and fully flatten the reservoir thus serving as an additional mounting means. Additional mounting means (not shown) may engage and grip the reservoir at other locations, e.g. along the welded edges 765.

Figure 22A:
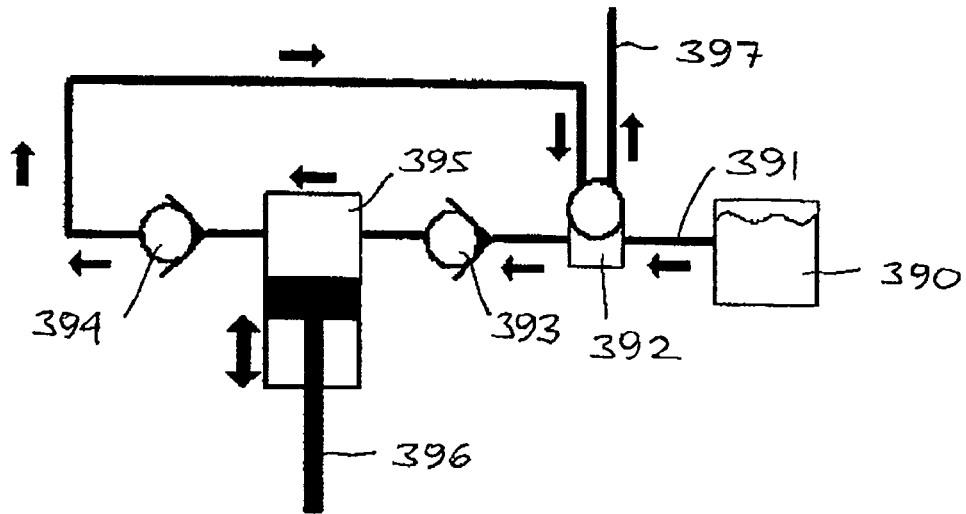
FIG. 22A shows a schematic overview of a pump connected to a reservoir.

With reference to FIG. 22A a schematic overview of a pump connected to a reservoir is shown, the pump comprising the following general features: a fluid connection 391 to reservoir a reservoir 390, a safety valve 392, inlet and outlet valves 393, 394, a pump chamber 395 with an associated piston 396, and an outlet 397. The arrows indicate the flow direction between the individual components. When the piston is moved downwards (in the drawing) a relative negative pressure will build up inside the pump chamber which will cause the inlet valve to open and subsequently fluid will be drawn form the reservoir through the open primary side of the safety valve. When the piston is moved upwards (in the drawing) a relative overpressure will build up in the pump chamber which will cause the inlet valve to close and the outlet valve and the safety valve to open whereby fluid will flow from the pump chamber through the outlet valve and the secondary side of the safety valve to the outlet. As appears, in normal operation the safety valve allows fluid passage during both intake and expelling of fluid and is thus "passive" during normal operation. However, in case the reservoir is pressurized (as may happen for a flexible reservoir) the elevated pressure in the reservoir will be transmitted to both the primary side of the safety valve and, via the pump chamber, the secondary side of the safety valve in which case the pressure on the primary side of the safety valve will prevent the secondary side to open.

Figure 22B:
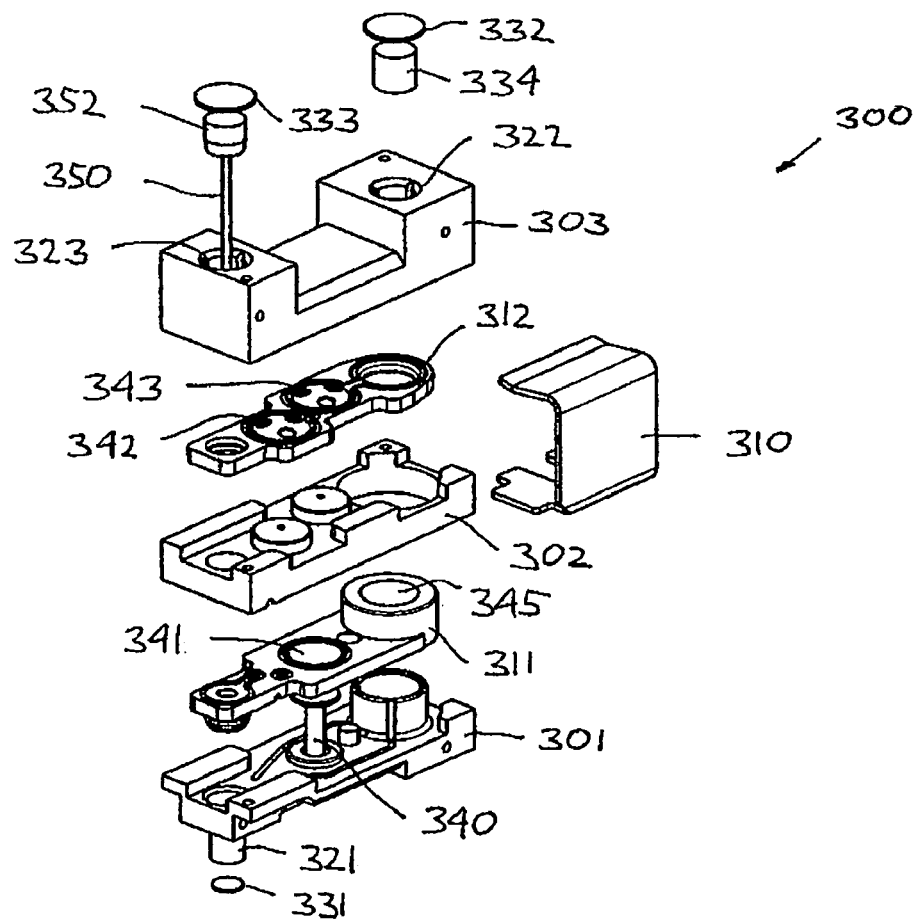
FIG. 22B shows an exploded view of a pump assembly.
Figure 22C:
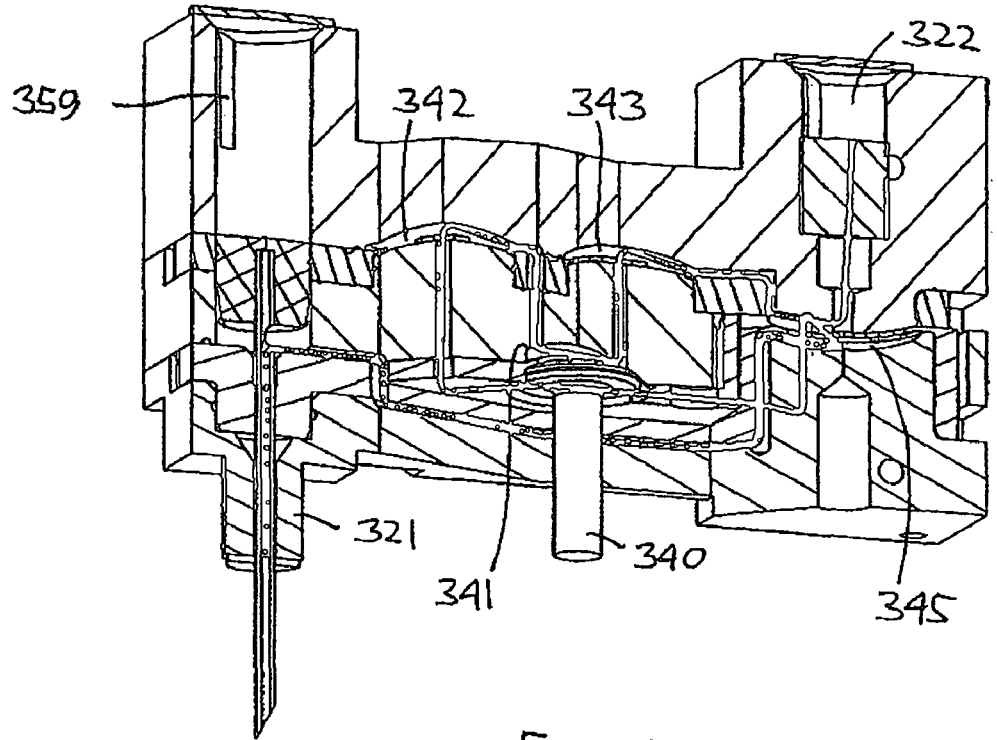
FIG. 22C shows a cross-sectional view of the pump assembly of FIG. 22C, FIGS. 22D and 22E show partial cross-sectional views of the pump assembly of FIG. 22C, FIGS. 23A and 23B show in a schematic representation a transcutaneous device in the form of a cannula and insertion needle combination.

In FIG. 22B an exploded view of a pump assembly 300 utilizing the pump principle depicted in FIG. 22A is shown, the pump assembly (in the following also referred to as a pump) being suitable for use with the reservoir units of FIGS. 1-13. The pump is a membrane pump comprising a piston-actuated pump membrane with flow-controlled inlet- and outlet-valves. The pump has a general layered construction comprising first, second and third members 301, 302, 303 between which are interposed first and second membrane layers 311, 312, whereby a pump chamber 341 is formed by the first and second members in combination with the first membrane layer, a safety valve 345 is formed by the first and third members in combination with the first membrane layer, and inlet and outlet valves 342, 343 are formed by the second and third members in combination with the second membrane layer (see FIG. 22C). The layers are held in a stacked arrangement by an outer clamp 310. The pump further comprises an inlet 321 and an outlet 322 as well as a connection opening 323 which are all three covered by respective membranes 331, 332, 333 sealing the interior of the pump in an initial sterile state. The membranes are penetratable or breakable (e.g. made from paper) by a needle or other member introduced through a given seal. The outlet further comprises a self-sealing, needle-penetratable septa 334 (e.g. of a rubber-like material) allowing the pump to be connected to an outlet needle. As shown in FIG. 22C a fluid path (indicated by the dark line) is formed between the inlet 321 (see below) and the inlet valve 342 via the primary side of the safety valve 345, between the inlet valve, pump chamber 345 and the outlet valve 343, and between the outlet valve and the outlet 322 via the secondary side of the safety valve, the fluid paths being formed in or between the different layers. The pump also comprises a piston 340 for actuating the pump membrane, the piston being driven by external driving means (not shown).

Figure 22D:
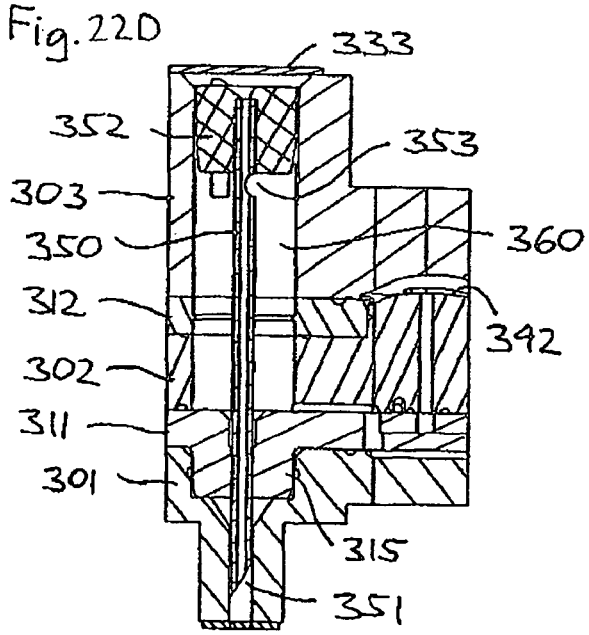

The pump further comprises a fluid connector in the form of hollow connection needle 350 slidably positioned in a needle chamber 360 arranged behind the connection opening, see FIG. 22D. The needle chamber is formed through the layers of the pump and comprises an internal sealing septum 315 through which the needle is slidably arranged, the septum being formed by the first membrane layer. The needle comprises a pointed distal end 351, a proximal end on which is arranged a needle piston 352 and a proximal side opening 353 in flow communication with the distal end, the needle and the piston being slidably arranged relative to the internal septum and the chamber. As can be appreciated form FIG. 22D the needle piston in its initial position is bypassed by one or more radially placed keyways 359. These are provided in order to allow steam sterilisation and to vent the air otherwise trapped when the fluid connector is moved forward in the needle chamber.

Figure 22E:
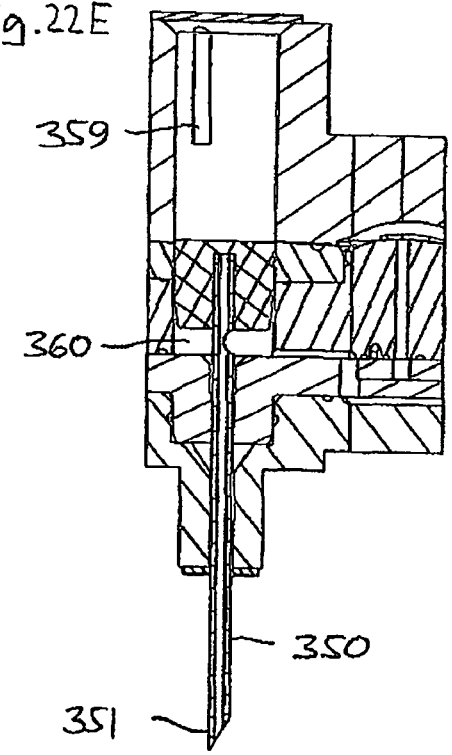

The above-described pump assembly may be provided in a drug delivery device of the type shown in FIGS. 1-20. In a situation of use where the reservoir unit is attached to a needle unit the proximal end 532 of the infusion needle is introduced through the outlet seal and septum 334 of the pump, and the actuator 515 (see FIG. 19) is introduced through the connection membrane 333. By this action the connection needle is pushed from its initial position as shown in FIG. 22D to a actuated position as shown in FIG. 22E in which the distal end is moved through the inlet membrane 331 and further through the needle-penetratable septum of a nearby located reservoir, this establishing a flow path between the reservoir and the inlet valve via the proximal opening 353 in the needle. In this position a seal is formed between the needle piston and the needle chamber.

As appears, when the two units are disconnected, the proximal end 532 of the infusion needle is withdrawn from the pump outlet whereas the connection needle permanently provides fluid communication between the pump and the reservoir.

In the above described embodiments, the transcutaneous device has been in the form of a unitary needle device (e.g. an infusion needle as shown or a needle sensor (not shown)), however, the transcutaneous device may also be in the form of a cannula or a sensor in combination with an insertion needle which is withdrawn after insertion thereof. For example, the first needle portion may be in the form of a (relatively soft) infusion cannula (e.g. a Teflon® cannula) and a there through arranged removable insertion needle. This type of cannula needle arrangement is well known from so-called infusion sets, such infusion sets typically being used to provide an infusion site in combination with (durable) infusion pumps.

Figure 23A:
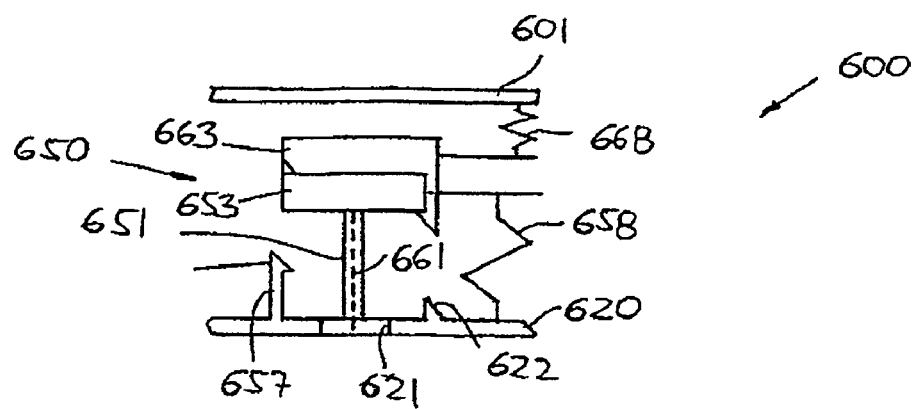
Figure 23B:
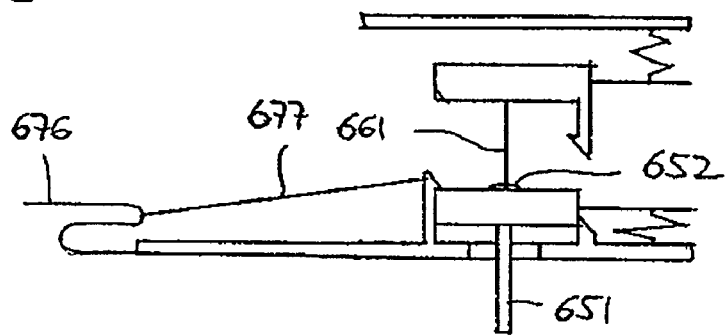

Thus, FIGS. 23A and 23B show in a schematic representation how a cannula and insertion needle combination can be arranged within a housing 601 of in a given medical device 600 (partly shown), e.g. an infusion device or an infusion set. More specifically, the medical device comprises a transcutaneous assembly 650 comprising a combination of a relatively soft cannula 651 (which e.g. may be of the soft "Teflon®" type) carried by a lower member 653 and a pointed insertion needle 661 (e.g. made from medical grade stainless steel) slidably arranged within the cannula and carried by an upper member 663, both members being mounted to allow axial displacement of the cannula respectively the insertion needle. The cannula comprises a proximal inlet (not shown) allowing it to be or to be arranged in fluid communication with a fluid source. The medical device further comprises a base plate 620 with an opening 621 for the cannula as well as a release member 622. The lower member comprises an elastomeric seal 652 through which the insertion needle is arranged. The cannula and the insertion needle may be straight or curved dependent upon how the two members are mounted in the device, e.g. arcuate corresponding to a pivoting axis or straight corresponding to linear movement as illustrated. The upper member comprises a coupling member 667 locking the members together in an initial position with distal end of the insertion needle extending from the distal opening of the cannula as shown in FIG. 23A, and the base plate comprises coupling member 657 for locking the lower member in an extended position with distal end of the cannula extending through the opening in the base plate (see FIG. 23B). Between the housing of the device and the upper member a first spring 668 is arranged biasing the upper member upwards. Correspondingly, the device also comprises a second spring 658 biasing the lower member upwardly. The medical device further comprises a gripping tab 676 and a pulling member 677 corresponding to the embodiment shown in FIG. 1.

In a situation of use the assembly is moved downwardly, either manually or by a releasable insertion aid, e.g. a spring loaded member acting through an opening in the housing (not shown) whereby the cannula with the projecting insertion needle is inserted through the skin of a subject. In this position the lower member engages the coupling member 657 to thereby lock the cannula in its extended position, just as the coupling member 667 is released by the release member 622 thereby allowing the upper member to return to its initial position by means of the first spring.

When the user intends to remove the delivery device from the skin surface, the user grips the gripping portion of the tab and pulls it in a first direction substantially in parallel with the skin surface, by which action the flexible strip 677 releases the coupling member 657 from the lower member whereby the lower member and thereby the cannula is retracted by means of the second spring. When the cannula has been withdrawn from the skin, the user uses the now unfolded tab to pull off the entire delivery device from the skin surface, for example by pulling the tab in a direction away from the skin surface.

Figure 24:
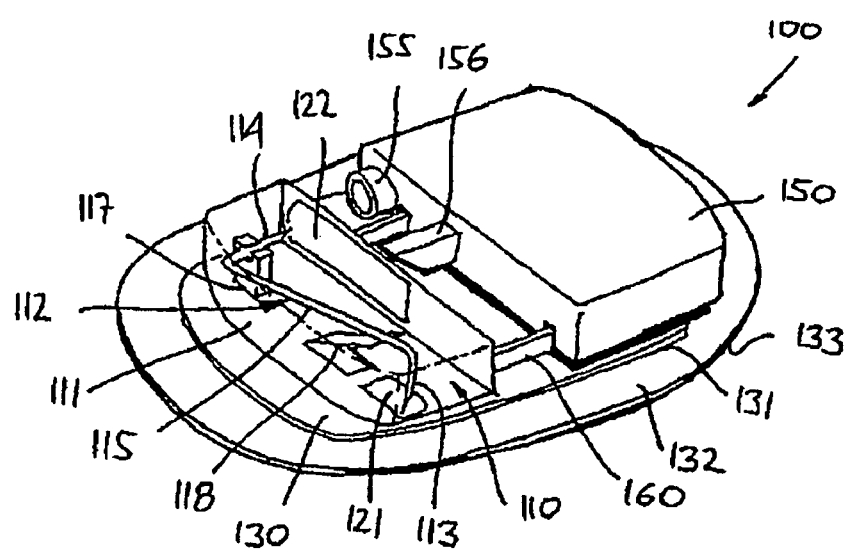
FIG. 24 shows a perspective view of a further drug delivery device.

In FIG. 24 an embodiment of a device adapted for the latter mounting procedure described with reference to FIGS. 1-12 is shown (i.e. mounting the needle unit first).

More specifically, FIG. 24 shows a perspective view of medical device in the form of a drug delivery device 100 comprising a needle housing 110, a base member 130 with a lower mounting surface 133 adapted for application to the skin of the subject, and a separate pump unit 150. In the shown embodiment the base member comprises a relatively rigid upper portion 131 attached to a more flexible adhesive patch member 132 having a lower adhesive surface providing the mounting surface per se. The needle housing may be formed integrally with the base member or attached thereto as a separate unit, the two elements in combination forming a platform unit. In the shown embodiment the needle unit comprises a housing 111 within which a hollow needle 112 is pivotally arranged.

The housing comprises first and second openings (or windows) covered by first and second cover means. In the shown embodiment the first cover means is in the form of a needle penetratable rubber membrane 121 and the second cover membrane is in the form of a breakable paper sheet allowing components to be introduced into the interior of the housing. The paper sheet is penetratable to sterilizing gases, the paper sheet, the rubber membrane and the housing in combination providing a sterility barrier for the encapsulated needle portion.

The needle comprises a first needle portion 113 having a first pointed end adapted to penetrate the skin of the subject, the first needle portion extending generally perpendicular to the mounting surface, and a second needle portion 114 in fluid communication with the first needle portion via an intermediate needle portion 115 and having a second pointed end, the second needle portion being arranged substantially in parallel with the mounting surface. The needle is connected to the housing by a mounting member 117 allowing the needle to pivot corresponding to an axis defined by the second needle portion, whereby the needle is moveable between an initial sterile position in which the first needle portion is retracted relative to the mounting surface, and a second position in which the pointed end of the first needle portion projects through the rubber septum and relative to the mounting surface. The housing also comprises a biasing member 118 biasing the needle towards the initial position. Often, the "downstream" portion of a needle (here: the first portion) is referred to as the distal portion, and the "upstream" portion of a needle (here: the second portion) is referred to as the proximal portion.

The reservoir (or pump) unit 150 comprises a housing in which a reservoir and expelling means are arranged. The reservoir is adapted to contain a liquid drug (e.g. prefilled or adapted to be filled by a user) and comprises an outlet means in the form of a protruding needle penetratable septum 155 adapted to be arranged in fluid communication with the second needle portion. The expelling means (not shown) is adapted for in a situation of use to expel a drug out of the reservoir and through the skin of the subject via the hollow needle. The pump unit further comprises a ramp member 156 arranged next to the reservoir outlet. The reservoir and expelling means may be of any suitable configuration, e.g. as disclosed with reference to FIGS. 25A-25D.

The mounting platform comprises a receiving portion, the receiving portion and the pump unit comprising mating coupling means 160 allowing the pump unit to be secured to the platform unit. The mating coupling means may be releasable allowing a durable or multi-use pump unit to be attached a number of times to a disposable platform unit.

In a situation of use, the platform unit is mounted on the skin of a user (e.g. by adhesive means arranged on the mounting surface) and the pump unit is attached and locked to the platform unit by sliding it into engagement therewith substantially in parallel with the mounting surface. During the latter operation the protruding septum and the ramp member is moved into engagement with the needle, thereby breaking the paper barrier cover 122, during which operation fluid communication is established between the second needle portion and the reservoir, just as the needle is pivoted from its initial to its second position, the first pointed needle end thereby penetrating the rubber membrane and the skin of the user.

After the pump unit has been connected and the needle introduced subcutaneously, the pump can be started. This may happen either automatically as the two units are connected or by separate user-actuatable starting means, e.g. a start button (not shown).

In an alternative embodiment (not shown), the second needle portion may be fixedly (i.e. non-rotationally) attached to the mounting member 117, the intermediate needle portion 115 being elastically bend as it is forced downwardly by the ramp member 156. In such an arrangement the biasing member 118 may be dispensed with.

In the above-described embodiments a delivery device has been described comprising a flexible reservoir in combination with an example of an expelling means. However, the reservoir and the expelling means may be of any type which would be suitable for arrangement within a skin-mountable drug delivery device. Further, as the needle of the present invention also may be in the form of a needle sensor, the interior of the medical device may comprise sensor means adapted to cooperate with the needle sensor.

Figure 25A:
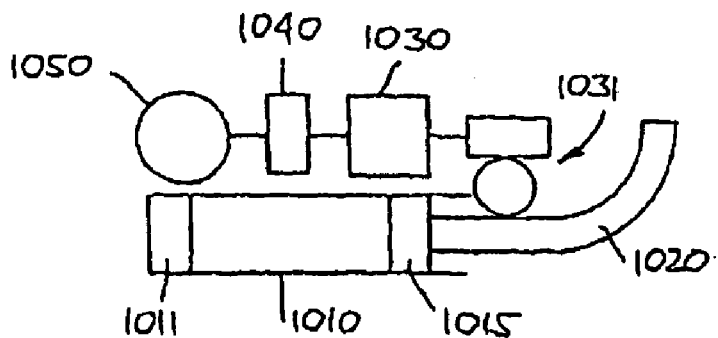
FIGS. 25A-25D show different expelling means suitable for use with the invention.

In FIGS. 25A-25E examples of expelling means suitable for use with the present invention are shown schematically, however, these are merely examples, just as the shown arrangement of the individual components not necessarily are suitable for direct application in the above shown delivery devices. More specifically, FIG. 25A shows a pump arrangement comprising a drug-containing cartridge 1010 forming a reservoir and having a distal closure member 1011 allowing a needle to be connected, and a piston 1015 slidingly arranged there within, a flexible toothed piston rod 1020 (for example as disclosed in U.S. Pat. No. 6,302,869), an electric motor 1030 which via a worm-gear arrangement 1031 drives the piston rod to expel drug from the cartridge, the motor being controlled by control means 1040 and the energy for the control means and the motor being provided by a battery 1050. The pump may be activated when the needle is inserted (by means not shown) or by separate user-actuatable means (not shown) after the inserter has been detached form the delivery device.

Figure 25B:
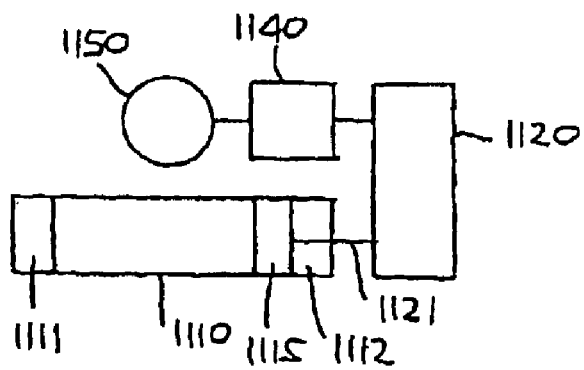

FIG. 25B shows a pump arrangement comprising a drug-containing cartridge 1110 having distal and proximal closure members 1111, 1112, and a piston 1115 slidingly arranged there within, gas generating means 1120 in fluid communication with the interior of the cartridge via conduit 1121 for driving the piston to expel drug from the cartridge, the gas generating means being controlled by control means 1140 and the energy for the control means and the gas generation being provided by a battery 1150. The pump may be activated as indicated above. A detailed disclosure of such gas generating means for a drug delivery device can be found in e.g. U.S. Pat. No. 5,858,001.

Figure 25C:
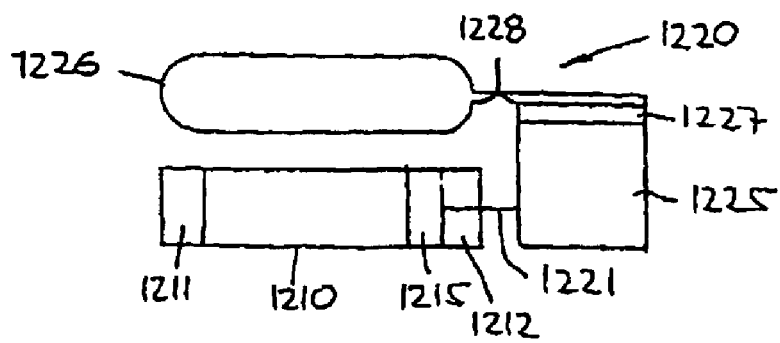

FIG. 25C shows a pump arrangement comprising a drug-containing cartridge 1210 having distal and proximal closure members 1211, 1212, and a piston slidingly 1215 arranged there within, an osmotic engine 1220 in fluid communication with the interior of the cartridge via conduit 1221 for driving the piston to expel drug from the cartridge. The osmotic engine comprises a first rigid reservoir 1225 containing a salt-solution and a second collapsible reservoir 1226 containing water, the two reservoirs being separated by a semi-permeable membrane 1227. When supplied to the user, the fluid connection 1228 between the second reservoir and the membrane is closed by a user-severable membrane (e.g. a weak weld) which, when severed, will allow the osmotic process to start as water is drawn from the second reservoir through the membrane and into the first reservoir. The pump may be activated as indicated above. A detailed disclosure of the osmotic drive principle can be found in e.g. U.S. Pat. No. 5,169,390.

Figure 25D:
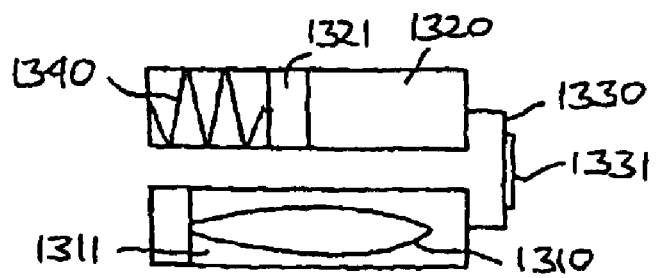

FIG. 25D shows a pump arrangement comprising a drug-containing flexible reservoir 1310 arranged within a rigid fluid-filled secondary reservoir 1311 in fluid communication with a primary reservoir 1320 through a conduit 1330 comprising a flow restrictor 1331. The primary reservoir is in the form of a cartridge with a moveable piston 1321 and contains a viscous drive fluid. A spring 1340 is arranged to act on the piston to drive fluid from the first to the second reservoir thereby expelling drug from the flexible reservoir when the latter is connected to an infusion needle (not shown). The flow rate will be determined by the pressure generated by the spring in the drive fluid, the viscosity of the drive fluid and the flow resistance in the flow restrictor (i.e. bleeding hole principle). The pump may be activated by straining the spring or by releasing a pre-stressed spring, either when the needle is inserted (by means not shown) or by separate user-actuatable means (not shown) after the inserter has been detached from the delivery device. An example of this principle used for drug infusion is known from DE 25 52 446. In an alternative configuration, the drug reservoir may be pressurized directly to expel the drug via a flow restrictor, e.g. as disclosed in U.S. Pat. No. 6,074,369.

Figure 26:
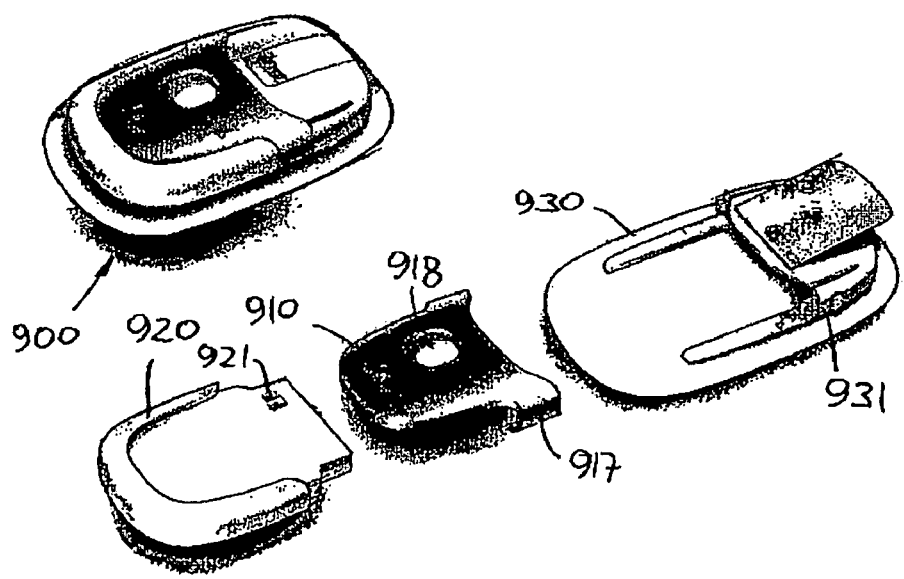
FIG. 26 shows a medical device with a modular reservoir unit.

In FIG. 26 is shown a medical device 900 corresponding to the embodiment of FIGS. 1-11, however, the reservoir unit has a modular design comprising a "durable" control unit 910 adapted to be mounted on a reservoir unit 920 comprising a reservoir and an expelling assembly controllable by the control unit through contacts 921. The transcutaneous device unit 930 may be the same as in FIGS. 1-11. The transcutaneous device unit and the reservoir unit comprise mating coupling means (931) allowing the reservoir unit to be secured to the transcutaneous device unit to provide fluid communication between the reservoir and the transcutaneous device, and the controller unit and the reservoir unit comprise mating coupling means (917, 921) allowing the controller unit to be secured to the reservoir unit to control the expelling assembly. The control unit may comprise one or more of the following features: a vibrator, a RF transmitter, a RF receiver, a display, a bolus button 918 (as shown) or other user input means, a back-up battery, a memory. Further, the control unit may be adapted to provide a fixed flow rate or it may be programmable (e.g. via a remote control) to provide a given rate or a given profile. The different control units may also be used with different reservoir units (e.g. comprising different drugs or different amounts of drugs), or with different needle units (e.g. comprising a needle or a soft cannula). As stated above, the controller may be used as a durable device by the user, however, (simpler) versions of the controller may come pre-attached to a reservoir unit and be used as a means to provide a varity of disposable devices.

Figure 27:
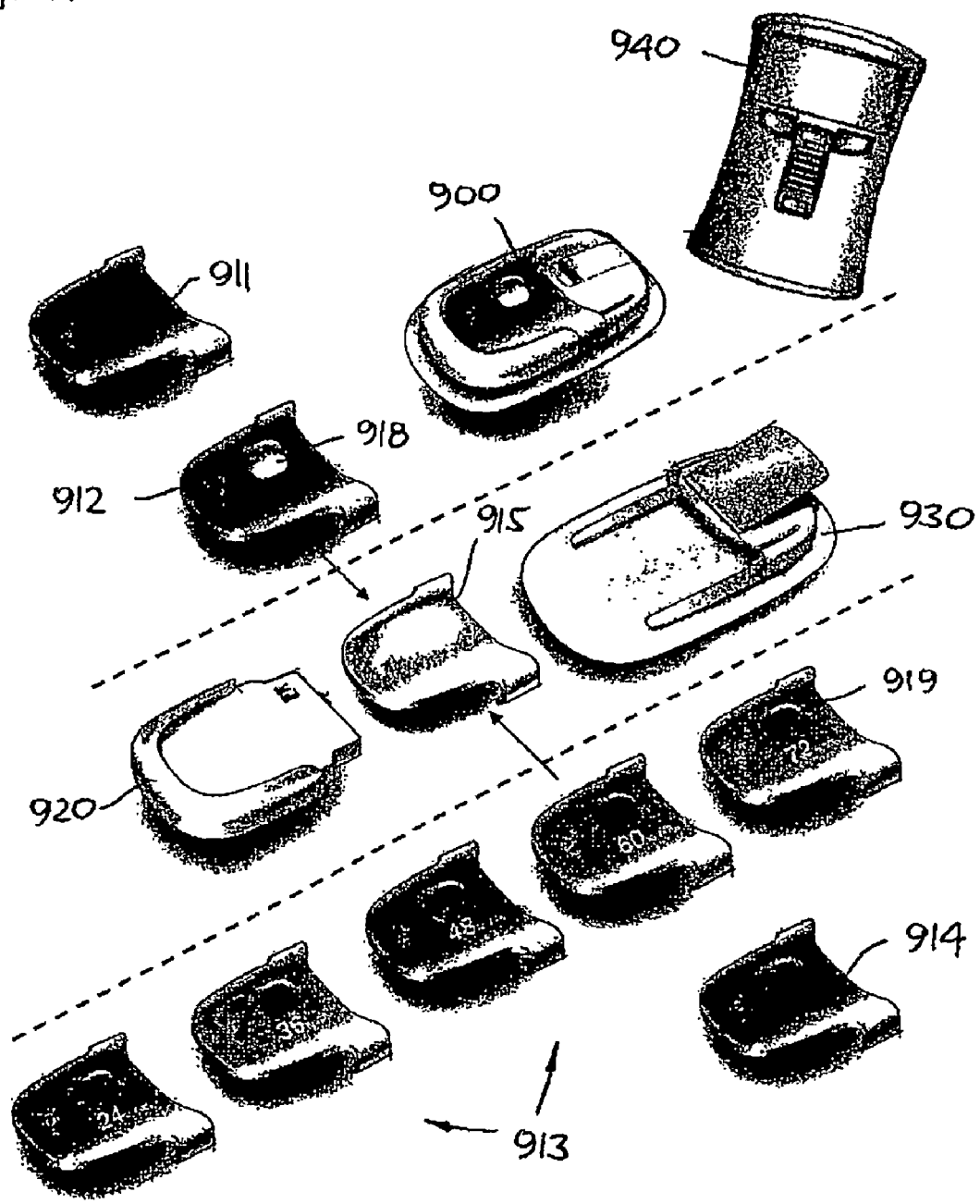
FIG. 27 shows a modular system for a medical device.

FIG. 27 shows a modular system comprising a number of different types of control units in addition to a basic needle patch unit 930 and a basic reservoir unit 920. A remote controller 940 may be used in combination with some of the control units. The control unit may be in the form of a remotely controllable unit 911 which can only be controlled from a remote controller. A variant 912 thereof may add a bolus button allowing the user to take a bolus of drug without having to use the remote controller. The control unit may be provided as a varity of preprogrammed control units 913, each providing a fixed flow rate as indicated on the unit. Such a unit is intended for use without a remote controller and may include a display 919 as shown. A programmable control unit 914 may also be provided, this allowing e.g. a medical practitioner to program the control unit for an individual patient. A dummy 915 represents any of the disclosed control units in combination with a reservoir unit and a needle unit.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A medical device, comprising a transcutaneous device unit and a separate reservoir unit, the transcutaneous device unit comprising:
   a transcutaneous device, and
   a mounting surface comprising a skin adhering adhesive,
      wherein the reservoir unit comprises:
   a reservoir adapted to contain a fluid drug, and
   an expelling assembly adapted for cooperation with the reservoir to expel fluid drug out of the reservoir and through the skin of the subject via the transcutaneous device,
   wherein the transcutaneous device unit and the reservoir unit are secured to each other in a situation of use,
   wherein the expelling assembly is activated or allowed to be activated to deliver fluid from the reservoir when the transcutaneous device unit and the reservoir unit are secured to each other and de-activated to stop fluid flow from the reservoir when the units are released from each other, and
   wherein the activation occurs by engaging an actuator on the transcutaneous device unit and deactivation occurs by disengaging the actuator.

2. A medical device as defined in claim 1, wherein fluid communication between the transcutaneous device and the reservoir is established when the transcutaneous device unit and the reservoir unit are secured to each other.

3. A medical device as in claim 1, wherein the expelling assembly is activated or allowed to be activated when the transcutaneous device unit and the reservoir unit are secured to each other and de-activated when the units are released from each other.

4. A medical device as defined in claim 1, wherein the expelling assembly comprises a pump having an inlet adapted to be arranged in fluid communication with the reservoir, and an outlet adapted to be arranged in fluid communication with the transcutaneous device, thereby allowing the transcutaneous device to be arranged in fluid communication with the interior of the reservoir.

5. A medical device as defined in claim 4, wherein the pump comprises an internal flow path arranged between the inlet and the outlet, the inlet and the outlet sealing the interior of the pump and thereby the flow path in an initial sterile state.

6. A medical device as defined in claim 5, wherein the reservoir unit is transformable from an initial condition in which there is no fluid communication between the pump and the reservoir to a non-reversible operating condition in which fluid communication is established between the inlet of the pump and the reservoir when the pump unit is secured to a transcutaneous device unit for the first time.

7. A medical device as defined in claim 6, wherein a fluid connector is arranged within the interior of the pump in the initial condition, the fluid connector comprising an inlet and an outlet, wherein the fluid connector is arranged to be operated from the initial condition and to an operating condition in which fluid communication is established between the interior of the reservoir and the interior of the pump via the fluid connector and with the outlet of the fluid connector being arranged in the flow path of the pump.

8. A medical device as defined in claim 7, wherein the fluid connector comprises a pointed inlet end, the reservoir comprising a penetratable portion allowing the pointed fluid connector inlet end to be inserted there through.

9. A medical device of claim 1, wherein the transcutaneous device comprises a pointed end adapted to penetrate the skin of a subject, the pointed end being moveable between an initial position in which the pointed end is retracted relative to the mounting surface, and an extended position in which the pointed end projects relative to the mounting surface.

10. A medical device as defined in claim 9, wherein the transcutaneous device unit comprises a further actuator for moving the pointed end of the transcutaneous device between the initial and the extended position when the actuator is actuated.

11. A medical device as defined in claim 10, wherein the transcutaneous device unit comprises an assembly for blocking the actuator, the blocking assembly being released when the transcutaneous device unit and the reservoir unit are secured to each other, thereby allowing the actuator to be actuated.

12. A medical device as defined in claim 10, wherein the expelling assembly is activated when the actuator is actuated.

13. A medical device as defined in claim 12, wherein the pointed end of the transcutaneous device is moveable between the extended position in which the pointed end projects relative to the mounting surface, and a retracted position in which the pointed end is retracted relative to the mounting surface.

14. A medical device as defined in claim 13, further comprising a retraction component for moving the pointed end of the transcutaneous device between the extended and the retracted position when the retraction components is actuated.

15. A medical device as defined in claim 14, wherein the actuator in an initial condition covers the retraction means, actuation of the actuator uncovering the retraction component.

16. A medical device as defined in claim 14, wherein the expelling assembly is deactivated when the retraction component is actuated.

17. A medical device as defined in claim 1, wherein the transcutaneous device comprises a first portion having a/the pointed end, and a second portion in fluid communication with the first portion and having a second end.

18. A medical device as defined in claim 17, wherein the second end comprises a pointed needle end, the outlet of the pump comprising a needle-penetratable septum allowing a fluid communication to be established between the second end of the transcutaneous device and the interior of the pump.

19. A medical device as defined in claim 1, wherein the mounting surface comprises adhesive allowing the medical device to be attached to a skin surface of the subject.

20. A medical device as defined in claim 19 when dependent upon claim 14, wherein operation of the retraction component from a first to an intermediate condition causes the transcutaneous device to be moved from the extended position to the retracted position, and operation of the retraction component from the intermediate to a second condition causes release of the device from the skin surface.

21. A medical device as defined claim 1, comprising releasable coupling for securing the transcutaneous device unit and the reservoir unit to each other.

22. A medical device as defined in claim 21, wherein the expelling assembly is deactivated when the two units are released from each other.

23. A medical device as in claim 1, wherein the reservoir is prefilled with a liquid drug.

24. A medical device as in claim 1, wherein the reservoir, in a situation of use, comprises a liquid drug but substantially no enclosed free gas.

* * * * *